US012004971B2

(12) United States Patent
Rouse et al.

(10) Patent No.: US 12,004,971 B2
(45) Date of Patent: Jun. 11, 2024

(54) MULTI PATH BIOMIMETIC AND VARIABLE STIFFNESS ANKLE SYSTEM AND RELATED METHODS

(71) Applicants: The Regents of the University of Michigan, Ann Arbor, MI (US); REHABILITATION INSTITUTE OF CHICAGO, Chicago, IL (US); Northwestern University, Evanston, IL (US)

(72) Inventors: Elliott J. Rouse, Ann Arbor, MI (US); Maxwell Shepherd, Evanston, IL (US); Hashim Quraishi, Ann Arbor, MI (US); Leo Mcmanus, Ann Arbor, MI (US)

(73) Assignees: The Regents of the University of Michigan, Ann Arbor, MI (US); REHABILITATION INSTITUTE OF CHICAGO, Chicago, IL (US); Northwestern University, Evanston, IL (US)

( * ) Notice: Subject to any disclaimer, the term of this patent is extended or adjusted under 35 U.S.C. 154(b) by 830 days.

(21) Appl. No.: 17/057,406

(22) PCT Filed: May 22, 2019

(86) PCT No.: PCT/US2019/033555
§ 371 (c)(1),
(2) Date: Nov. 20, 2020

(87) PCT Pub. No.: WO2019/226789
PCT Pub. Date: Nov. 28, 2019

(65) Prior Publication Data
US 2021/0307938 A1    Oct. 7, 2021

Related U.S. Application Data

(60) Provisional application No. 62/674,882, filed on May 22, 2018.

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 2002/507* (2013.01);
(Continued)

(58) Field of Classification Search
CPC ..... A61F 2/66; A61F 2/6607; A61F 2002/507
See application file for complete search history.

(56) References Cited

U.S. PATENT DOCUMENTS 2,638,605 A    5/1953 Johnson
9,393,131 B2 *  7/2016 Evans ..................... A61F 2/585
(Continued)

OTHER PUBLICATIONS

International Search Report and Written Opinion for PCT/US2019/033555, dated Aug. 12, 2019, 13 pages.

*Primary Examiner* — Brian A Dukert
(74) *Attorney, Agent, or Firm* — Casimir Jones, S.C.; Tanya A. Arenson

(57) ABSTRACT

A cam system for an assistive device and related methods are disclosed. The cam system may comprise a multi (e.g., dual) cam profile and a cam follower.

19 Claims, 20 Drawing Sheets

(51) Int. Cl.
*A61F 2/50* (2006.01)
*A61F 2/68* (2006.01)

(52) U.S. Cl.
CPC ............. *A61F 2002/6657* (2013.01); *A61F 2002/6863* (2013.01); *A61F 2002/701* (2013.01)

(56) References Cited

U.S. PATENT DOCUMENTS

| | | |
|---|---|---|
| 9,443,203 B2 | 9/2016 | Young et al. |
| 2010/0298102 A1 | 11/2010 | Bosecker et al. |
| 2013/0268095 A1 | 10/2013 | Evans et al. |
| 2015/0230943 A1 | 8/2015 | Marlin et al. |
| 2017/0173783 A1 | 6/2017 | Angold et al. |
| 2018/0085237 A1 | 3/2018 | Gao et al. |
| 2018/0092761 A1 | 4/2018 | Rouse et al. |

\* cited by examiner

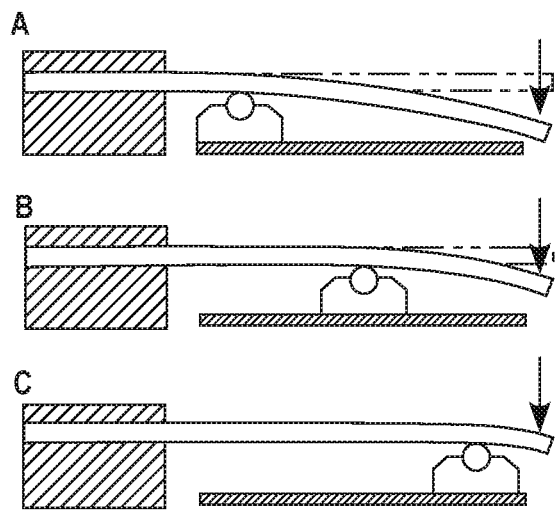
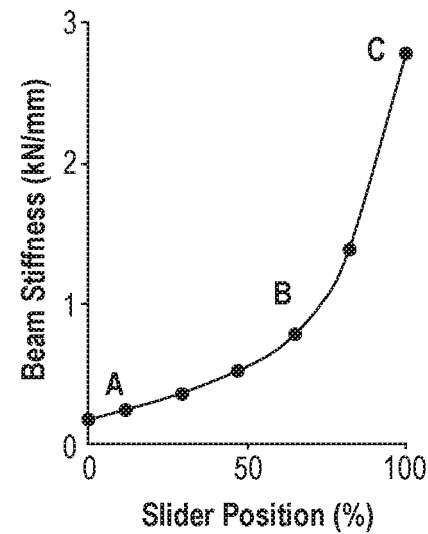
FIG. 4A
FIG. 4B
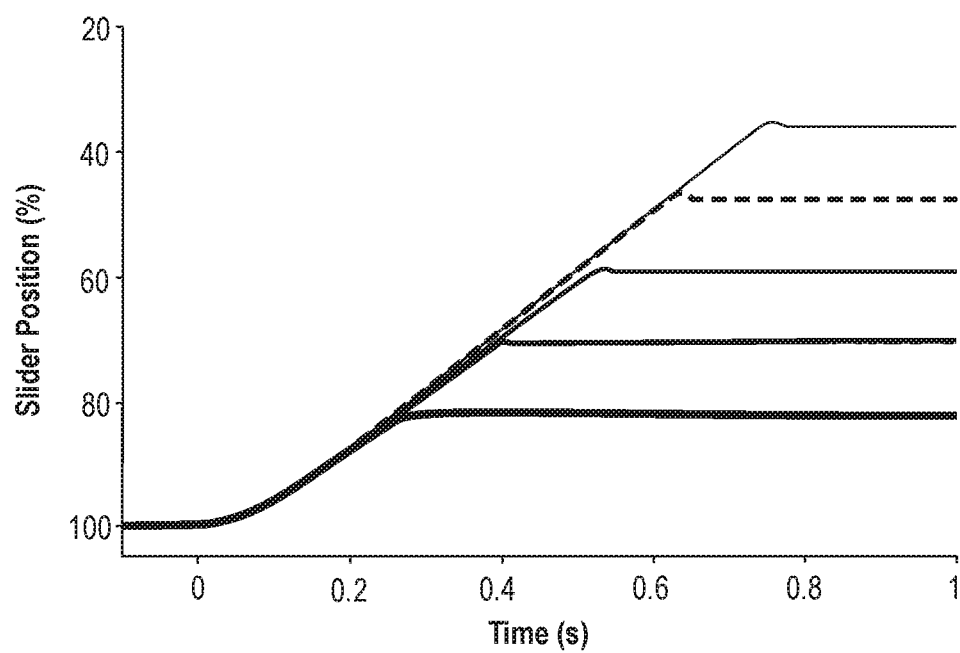
FIG. 5

FIG. 13
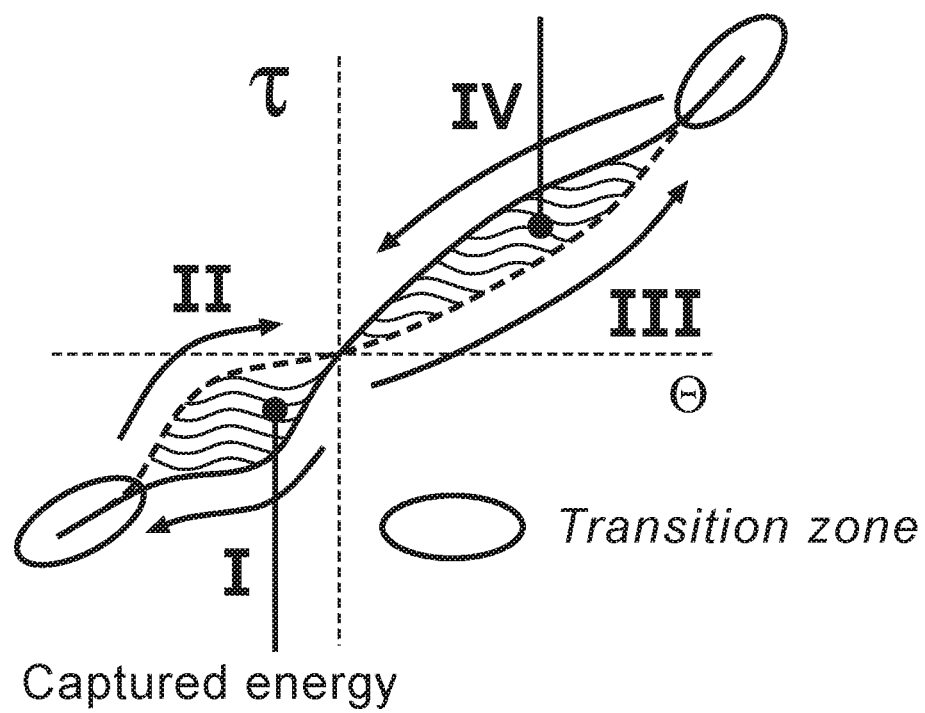
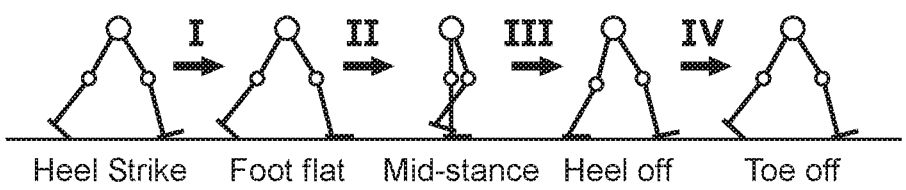

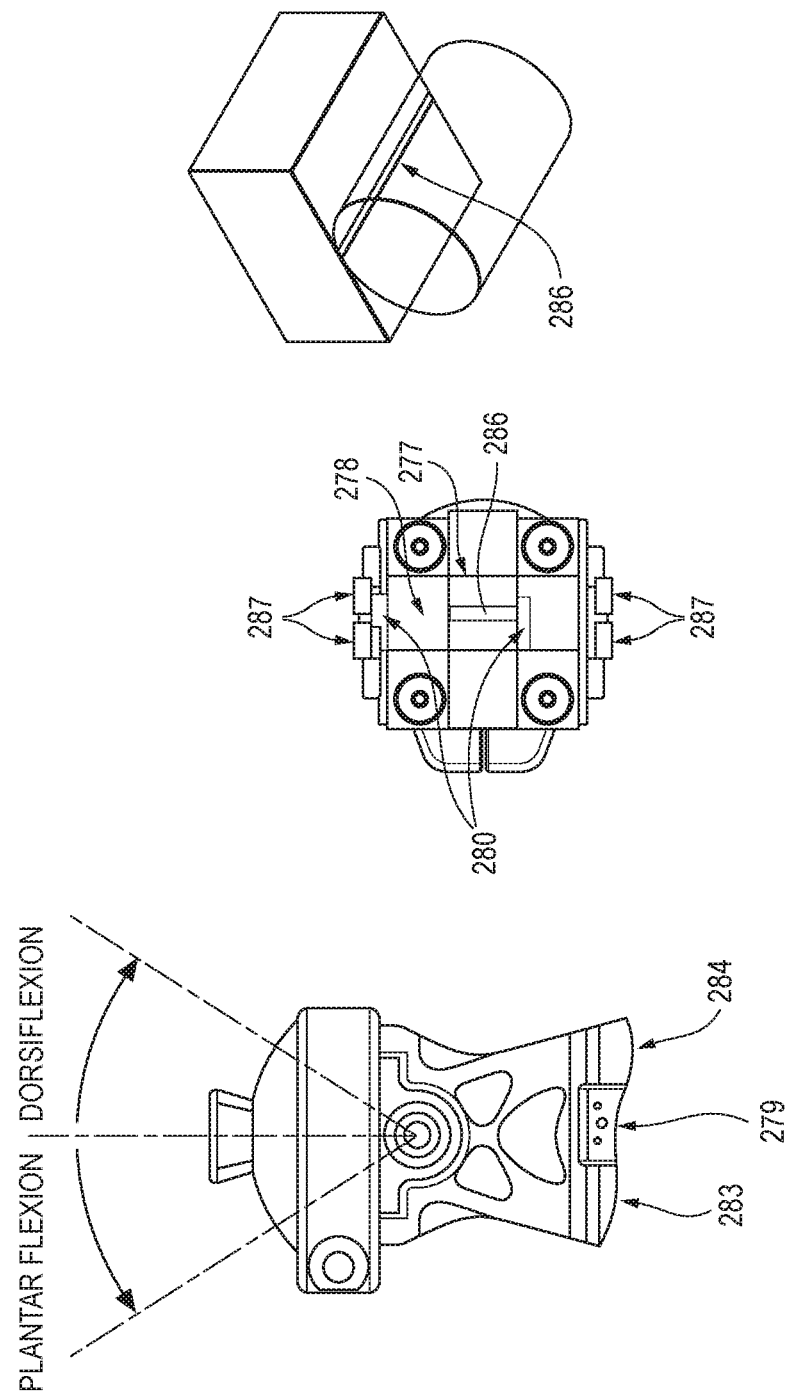

ized component to switch the follower between cam profiles.

MULTI PATH BIOMIMETIC AND VARIABLE STIFFNESS ANKLE SYSTEM AND RELATED METHODS

This application is a national phase application under 35 U.S.C. § 371 of PCT International Application No. PCT/US2019/033555, filed May 22, 2019, which claims priority to U.S. provisional patent application Ser. No. 62/674,882, filed May 22, 2018, which is incorporated herein by reference in its entirety.

STATEMENT REGARDING FEDERALLY SPONSORED RESEARCH OR DEVELOPMENT

This invention was made with government support under W81XWH-17-1-0704 awarded by the U.S. Army Medical Research and Development Command. The government has certain rights in the invention.

FIELD

Provided herein is a cam system for an assistive device and related methods. In particular, provided herein is a cam system comprising a multi (e.g., dual) cam profile and a cam follower.

BACKGROUND

Ankle-foot prostheses are used by individuals who do not have an ankle. Many commercially available prosthetic ankle-feet behave much like springs, storing and returning energy to the wearer. However, the torque-angle relationships of these prostheses do not appropriately follow the torque-angle relationship (or "quasi-stiffness" curve) of able-bodied walking.

Some ankle-foot prostheses, such as a Solid Ankle-Cushion Heel (SACH) Foot, are stiffer during stance phase than a human ankle would be in a similar phase. Other ankle-foot prostheses, such as Energy Storage and Return (ESR) feet, are less stiff, but do not appropriately mimic the low quasi-stiffness during early stance, and the rapidly increasing quasi-stiffness before heel-off. This may in part be due to the difficulty of designing devices with nonlinear stiffness characteristics. As a result of the relatively high stiffness during mid-stance of such prostheses, the individual's tibial progression is hindered, which may slow the self-selected walking speed. The relatively high stiffness of such prostheses during controlled plantarflexion immediately following heel strike may also prolong heel-only contact, reducing stability and inhibiting tibial progression.

ESR feet are also unable to modulate their mechanical properties to improve function during other mobility tasks. For instance, during quiet standing, transtibial amputees exhibit increased postural sway. Additionally, ESR feet exhibit significantly reduced range of motion during stair traversal, likely due to their high stiffness making forward progression of the center of mass more difficult. In addition, they are unable to capture the change in potential energy of the center of mass that results from tibial progression. For these tasks, amputees develop abnormal compensatory gait patterns which can lead to a wide range of issues, such as socket pain, back pain, and joint diseases.

Some ankle prostheses vary damping characteristics. Changing ankle mechanics with damping variation may be counterproductive, since energy is being removed from the ankle joint, which provides a majority of the mechanical energy needed for forward propulsion in able-bodied gait.

It would be useful for an ankle-foot prosthesis to exhibit appropriate biomechanics during various phases of gait, such as walking, stair traversal, or quiet standing. Likewise, it would be useful for other assistive devices, such as orthoses, to help patients exhibiting similarly appropriate biomechanics using their sound limbs.

BRIEF SUMMARY

A cam system for an assistive device is disclosed. The system may comprise a cam profile and a cam follower. The cam profile may have a curved outer edge comprising a concave portion. The cam follower may be positioned within the concave portion when the assistive device is in an equilibrium position.

The cam profile may be positioned to rotate about a joint of the assistive device in response to a force applied to the assistive device during a stance phase of gait.

The cam follower may be coupled to a leaf spring of the assistive device. The cam follower may roll along the curved outer edge of the cam profile from dorsiflexion to plantarflexion of the assistive device.

The cam profile may have a convex portion on which the cam follower is positioned during plantarflexion of the assistive device. The cam profile may have a convex portion on which the cam follower is positioned during dorsiflexion of the assistive device.

An assistive device comprising a cam system is disclosed. The assistive device may comprise a leaf spring. The cam system may be positioned at an end of the leaf spring such that a force applied to the cam system causes deflection of the leaf spring. The assistive device may comprise a sliding element to adjust the stiffness of the leaf spring upon deflection. The position of the sliding element may be adjustable along a surface of the leaf spring.

The sliding element may be positioned on a motor-powered screw that adjusts the position of the sliding element on the surface of the leaf spring. The position of the sliding element along the surface of the leaf spring may be manually adjustable. The assistive device may comprise a Bowden cable attached to the sliding element to manually adjust the position of the sliding element.

Certain embodiments provide a cam system comprising a multi (e.g., dual) cam profile and follower and uses thereof. The present disclosure is not limited to particular cam profiles. Any configuration where the follower takes a different path during energy storage compared to energy release, which allows the system to recycle and release energy different than how it was stored is specifically contemplated. For example, in some embodiments, provided is a cam system for an assistive device, comprising: a cam comprising at least two cam profiles (e.g., two distinct adjacent cam profiles or a cam surface comprising multiple paths); and a cam follower, wherein said cam follower switches between distinct cam profiles when the assistive device is in use. In some embodiments, the multiple cam profile component is configured to provide energy recycling and/or variations in energy return rate when the assistive device is in use.

The present disclosure is not limited to a particular configuration for switching between distinct cam profiles. Specifically contemplated are embodiments where one or more of the cam or cam follower components move relative to the other in order to switch the follower between cam profiles. In some embodiments, the cam comprises a cam profile slider and a stationary component, wherein the cam profile slider is configured to move relative to the stationary component. In some embodiments, the cam profile slider moves in the medio-lateral direction. In some embodiments, the cam follower is stationary. In some embodiments, the cam profile slider comprises a top surface and a bottom surface, wherein the bottom surface comprises the at least two cam profiles and contacts the cam follower and the top surface is in contact with the stationary component. In some embodiments, the multiple cam profiles each comprise a transition zone and a distinct zone. In some embodiments, the cam profile slider switches between the cam profiles when the transition zones of the distinct cam profiles are aligned.

The present disclosure is not limited to a particular switching component or method of switching. Both passive and active (e.g., via a transport component) are specifically contemplated. For example, in some embodiments, the cam profile comprises a transport component (e.g., one or more of a plurality of magnets, a solenoid, a pneumatic component, or a linkage component). In some embodiments, the transport component is at least two magnets. In some embodiments, the at least two magnets comprise two or more pairs of magnets (e.g., a pair of slider magnets adjacent the cam profile slider and at least one pair (e.g., at least two pairs) of frame magnets located on the stationary component. In some embodiments, the cam follower is a roller.

In some embodiments, provided is a dual cam system where the cam profiles are stationary and the cam follower (e.g., a spherical follower) moves between adjacent distinct cam profiles. In some embodiments, each of the at least two distinct adjacent cam profiles comprise a cam surface and the cam follower is positioned to roll along, and is switchable between, the cam surfaces of the at least two distinct adjacent cam profiles. In some embodiments, each of the at least two distinct adjacent cam profiles comprise a discrete path that comprises a groove provided within the cam profile. In some embodiments, the cam follower is spherical. In some embodiments, the cam follower is in a housing (e.g., comprising a cap). In some embodiments, the cam follower is positioned to roll along, and is switchable between, the discrete paths of the at least two distinct adjacent cam profiles.

The assistive device may be an ankle prosthesis or an orthosis.

BRIEF DESCRIPTION OF THE SEVERAL VIEWS OF THE DRAWINGS

The following descriptions of the drawings and example assistive devices present certain aspects, wherein like reference numerals across the several views refer to identical or equivalent features, and wherein:

FIG. 4A displays an illustration of how moving a simple support towards a load increases spring stiffness.

FIG. 4B displays a graph indicating experimental results of translational leaf spring stiffness as a function of the slider position.

FIG. 5 displays a graph that plots slider position as a percentage against time, depicting step responses from standing stiffness to other stiffnesses in an example of an ankle prosthesis.

FIG. 13 displays energy curves for captured and recycled energy during different phases of walking.

FIG. 18A displays cam profile switching during a step.

DETAILED DESCRIPTION

Figure 1:
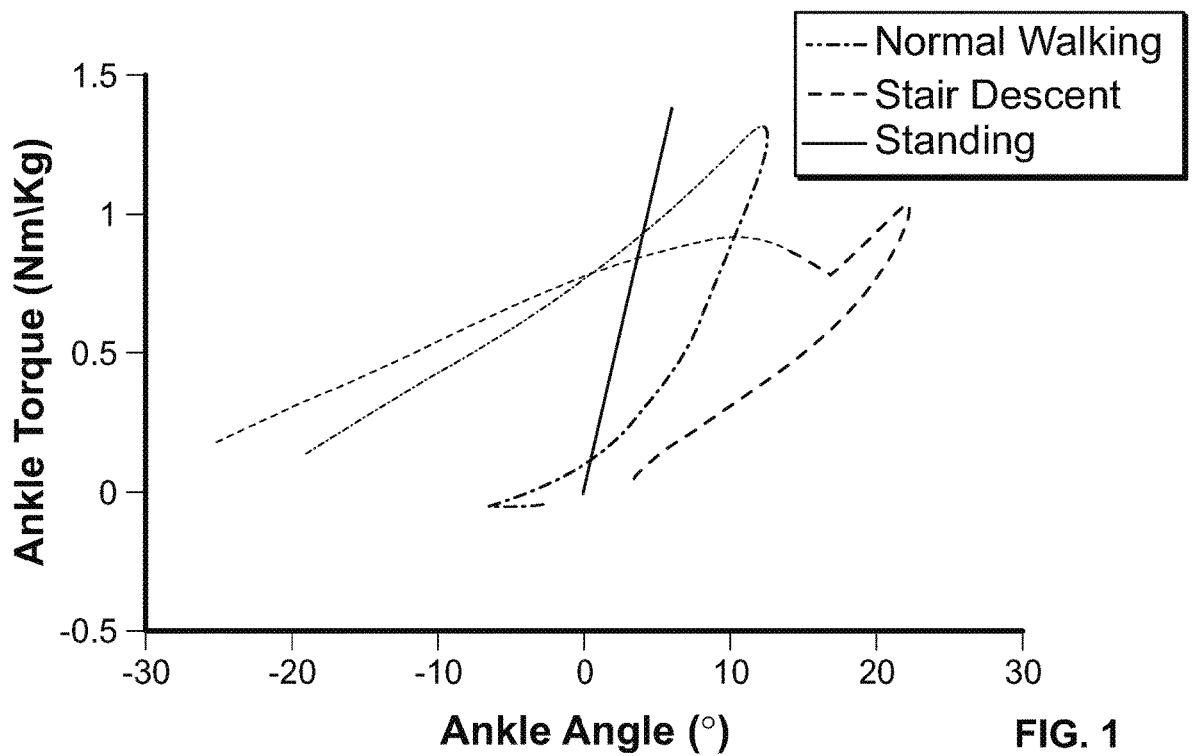
FIG. 1 displays a series of able-bodied ankle quasi-stiffness curves during stance phase, for level-ground walking, stair descent, and standing.

"Dorsiflexion" is the flexion of a human ankle or an assistive device such that the angle between the foot and shin decreases. In dorsiflexion, the toes on a human foot point upwards towards the shin. A "dorsiflexion position" is a position of the ankle or assistive device when it is in dorsiflexion.

"Plantarflexion" is the extension of a human ankle or an assistive device such that the angle between the foot and the shin increases. In plantarflexion, the toes on a human foot point away from the shin. A "plantarflexion position" is a position of the ankle or assistive device when it is in plantarflexion.

An "equilibrium position" refers to the position of an assistive device when the assistive device is between a dorsiflexion position and a plantarflexion position.

"Stance phase" of gait refers to the phase of gait when a foot or prosthesis is touching the ground during gait.

"Swing phase" of gait refers to the phase of gait when the foot or prosthesis has left the ground.

A "cam system" is an element of an assistive device or prosthesis that comprises a "cam" and a "cam follower." The cam system functions to provide rotation of the device around a point or axis (e.g., during gait).

A "cam" refers to an element of an assistive device or prosthesis comprising a curved surface or groove, which through rotation, oscillation, or reciprocation induces a predetermined motion of a second element, the second element referred to as a "cam follower." In some embodiments, the cam is the element that rotates about the axis/prosthetic ankle joint.

A "cam profile" is the curved surface or groove of the cam that contacts the "cam follower". In some embodiments, the cam profile comprises multiple (e.g., dual) distinct cam profiles with different shapes. In some embodiments, the multiple cam profiles are adjacent (e.g., side by side or another configuration). In some embodiments, cam profiles are provided as distinct paths (e.g., grooves) that contact the followed. In some embodiments, the multiple cam profiles are part of a cam surface that provides multiple paths or profiles on a continuous cam surface.

Example ankle prostheses disclosed herein are designed to closely match human biomechanics during gait. The ankle prosthesis may comprise a cam-based transmission and a stiffness modulation unit. The cam-based transmission may comprise a cam profile, a cam follower, and a spring. The stiffness modulation unit can be adjustable to adjust the stiffness of the spring in the cam-based transmission. The cam profile may be machined to create a specific torque-angle relationship depending on the adjustment of the stiffness modulation unit. As used herein, the phrase "primary stiffness modulation unit position" refers to a pre-determined position of the stiffness modulation unit, and the "primary stiffness curve" refers to a specific torque-angle relationship provided by the ankle prosthesis when the stiffness modulation unit is at the primary stiffness modulation unit position.

A quasi-passive ankle-foot prosthesis is disclosed. The prosthesis employs a customizable torque-angle profile for gait. The ankle stiffness can be varied continuously. The ankle-foot prosthesis may comprise a cam-based transmission, in which rotation of the ankle joint in the prosthesis causes a cam follower to deflect a leaf spring, and a repositionable sliding support beneath the leaf spring that can change the beam's stiffness. In a preferred example, the mechanism is lightweight and fits into an anthropomorphic physical envelope. Ankle stiffness may be adjusted during the swing phase of locomotion, as well as between ambulation modes such as between standing and stair traverse. The cam profile may be designed on the basis of a mathematical model to create a desired stiffness profile.

Quasi-passive ankle-foot prostheses are disclosed. An example prosthesis employs a customizable torque-angle profile for gait. The ankle stiffness can be varied continuously. The ankle-foot prosthesis may comprise a cam-based transmission, in which rotation of the ankle joint in the prosthesis causes a cam follower to deflect a leaf spring, and a repositionable sliding support beneath the leaf spring that can change the beam's stiffness. In a preferred example, the mechanism is lightweight and fits into an anthropomorphic physical envelope. Ankle stiffness may be adjusted during the swing phase of locomotion, and between ambulation modes. The cam profile may be designed on the basis of a mathematical model to create a desired stiffness profile.

An example passive ankle-foot prosthesis employs a customizable torque-angle profile for gait. The ankle stiffness can be varied continuously. The ankle-foot prosthesis may comprise a cam-based transmission, in which rotation of the ankle joint in the prosthesis causes a cam follower to deflect a leaf spring, and a repositionable sliding support beneath the leaf spring that can change the beam's stiffness. In a preferred example, the mechanism is lightweight and fits into an anthropomorphic physical envelope. Ankle stiffness may be adjusted during the swing phase of locomotion, and between ambulation modes. The cam profile may be designed on the basis of a mathematical model to create a desired stiffness profile.

FIG. 1 displays a series of able-bodied ankle quasi-stiffness curves during stance phase, for level-ground walking, stair descent, and standing. The bolded portions of each curve indicate controlled dorsiflexion for walking, and heel strike to toe-off for stair descent. Standing stiffness is an estimate of the purely passive ankle stiffness required to explain sway dynamics in quiet standing. Positive torque is plantarflexive, positive angle is dorsiflexion.

Figure 2A:
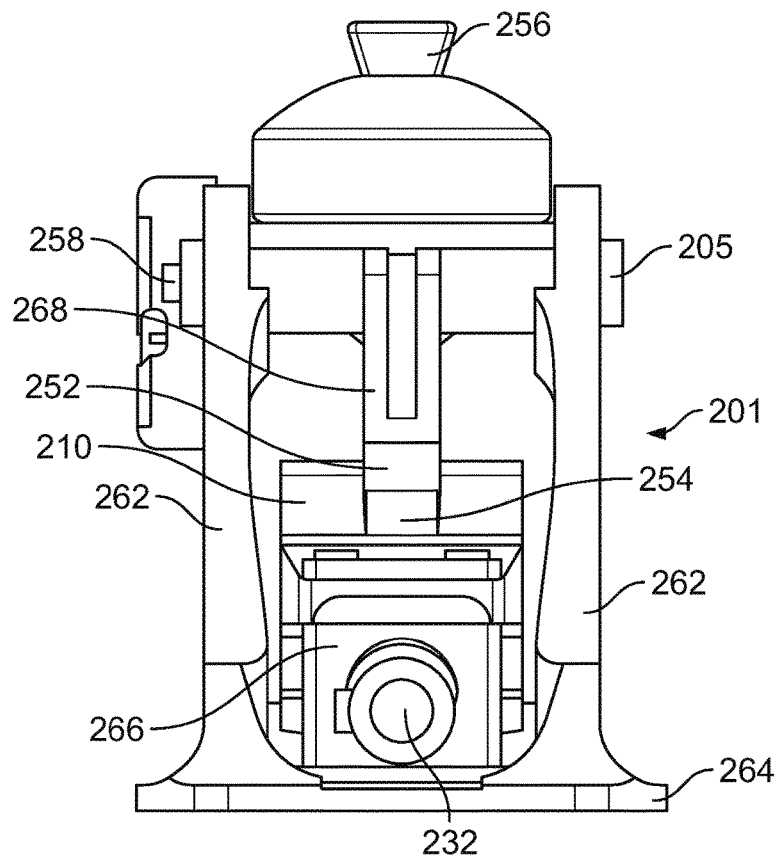
FIG. 2A displays a front view of an example ankle prosthesis.
Figure 2B:
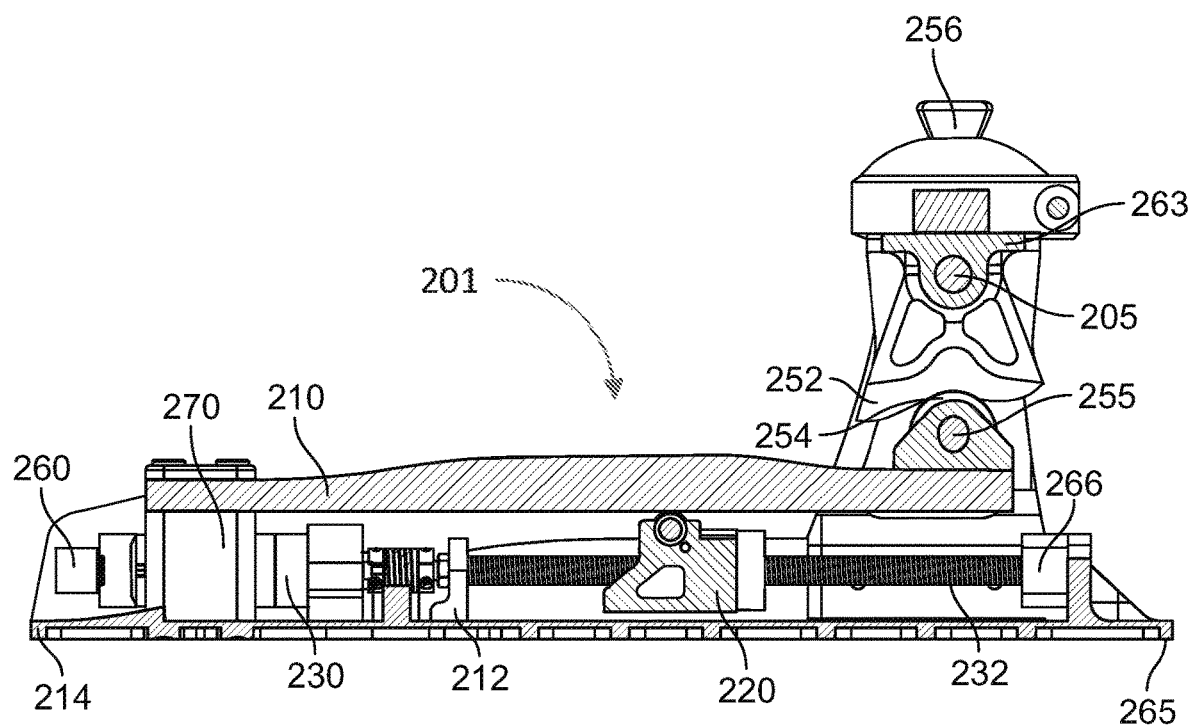
FIG. 2B displays a side view of an example ankle prosthesis.

FIGS. 2A and 2B display a front view and a side view, respectively, of an exemplary ankle prosthesis 201. The ankle prosthesis 201 comprises a cam-based transmission, in which a cam profile 252 at the ankle joint 205 compresses a leaf spring 210. In the example shown in FIGS. 2A and 2B, the stiffness modulation unit includes an attachment block 266, a lead screw 232, and a slider 220, which actively modifies the support conditions of the leaf spring 210 to affect stiffness. For ambulation modes other than walking, the slider 220 can be repositioned along the length of the lead screw 232 to modify the shape of the torque-angle relationship to be more or less stiff, deviating from the primary stiffness curve. When the slider 220 is positioned closer to the attachment block 266, the stiffness of the leaf spring 210 increases. When the slider 220 is positioned further from the attachment block 266, the stiffness of the leaf spring 210 decreases. The slider 220 may comprise a roller or other bearing system to reduce friction between the slider 220 and the leaf spring 210.

A user wearing the ankle prosthesis 201 causes the ankle prosthesis 201 to rotate about the ankle joint 205 by placing a load on the ankle prosthesis 201—for example, when the user is walking and places the heel 265 into contact with the ground, the user transfers his or her weight onto the ankle prosthesis 201. As the user applies such a force, the upper frame 263 begins to rotate about the ankle joint 205 with respect to the frame 262. A cam profile 252 is rigidly affixed to the upper frame 263, such that the cam profile 252 likewise rotates around the ankle joint 205. As the cam profile 252 rotates, a cam follower 254 rolls along a cam profile 252, both during dorsiflexion and plantarflexion of the ankle prosthesis 201. Rotation of the prosthesis 201 at the ankle joint 205 causes downward deflection of a cam follower 254, which causes deflection of the leaf spring 210. This deflection causes a restoring torque at the ankle joint 205.

Figure 2C:
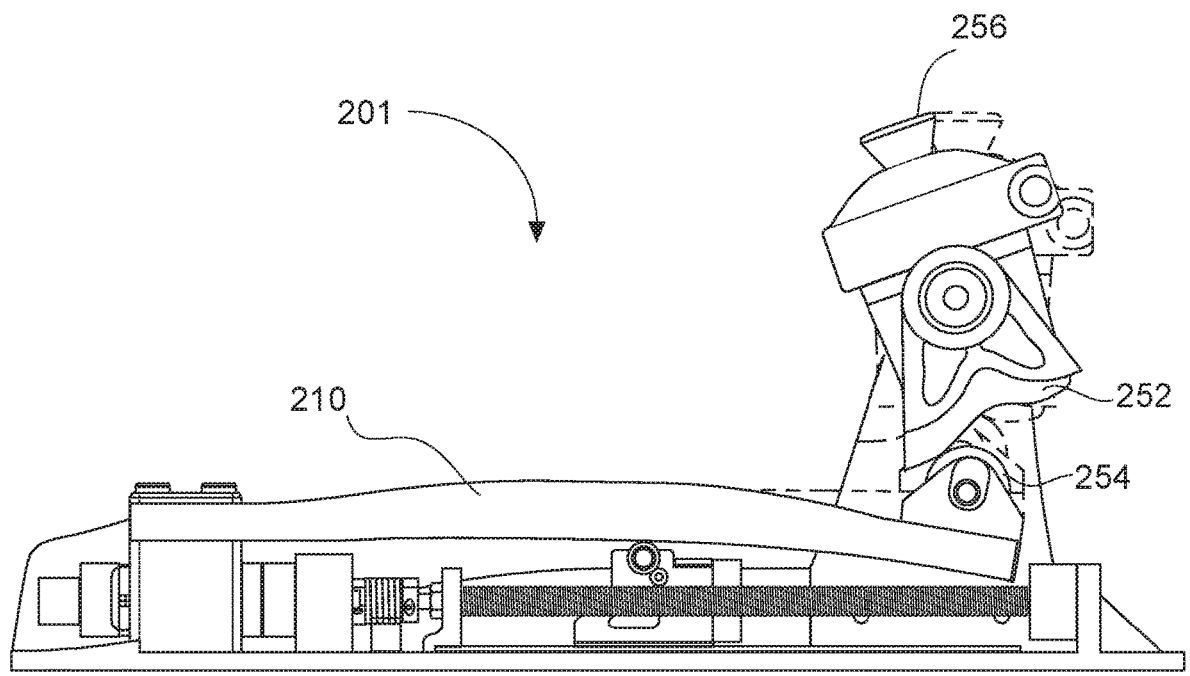
FIG. 2C displays another side view of the example ankle prosthesis.

FIG. 2C displays a side view of the prosthesis 201 in a dorsiflexion position, while the leaf spring 210 is under deflection. A force is applied to the upper portion of the prosthesis 201 comprising adaptor 256, which causes cam profile 252 to rotate about the ankle joint 205 205. Rotation of cam profile 252 applies a downward force on the proximal end of the leaf spring 210, causing the deflection of the leaf spring 210 shown in FIG. 2C.

Cam Design. The cam profile 252 governs the relationship between angle of the ankle prosthesis 201 at the ankle joint 205, and the associated deflection of the leaf spring 210 (thus, governing the ankle torque-angle). The cam profile 252 can be machined to create a specific torque-angle relationship for the ankle prosthesis 201 based on the primary slider position. Exemplary mathematics governing the relationship between a cam profile 252 and the ankle torque-angle curve are presented below.

In an example, a cam follower 254 has a diameter of 19 mm and a dynamic load rating of 4 kN (Misumi USA, Schaumburg Ill.). A cam profile 252 may be machined from an appropriate material, such as tool steel, which has a hardness and resistance to deformation. A cam profile 252 may be hardened to approximately 60 Rockwell C to prevent deformation from the high loads. The shape of a cam profile 252 corresponds to the primary stiffness curve, which mimics the able-bodied quasi-stiffness curve.

A cam profile 252 can be machined so that during a specific ambulation mode, such as walking, a cam profile 252 creates specific torque-angle relationship (the "primary stiffness curve") at a specified position of the slider 220 (the "primary slider position"). For other ambulation modes, the slider 220 can be repositioned to modify the shape of the torque-angle relationship to be more or less stiff, deviating from the primary stiffness curve, for different ambulation modes, such as standing or stair descent.

The loading and unloading torque-angle curves of a conventional spring-like prosthesis are identical, assuming there are no losses. This is also true for a cam-based transmission with a single cam profile. In contrast, in some embodiments, provided herein are prosthesis comprising multiple (e.g., dual or higher order) cam profiles. By using multiple cam profiles, the loading and unloading of the leaf spring 210 are decoupled. This allows for the energy storage and return to occur independent of each other, under the condition that the total amount of energy stored and returned is at most equal. The multi-cam profile systems described herein provide the advantage of energy recycling and/or variations in energy return.

FIG. 13 displays an example of energy recycling in a dual cam profile prosthesis. As shown in FIG. 13, energy is captured in the early stance phase and recycled in the late stance phase in order to enhance the push-off. The solid and striped line are two separate torque-angle curves, and a switch between these curves occurs in the transition zone, where the curves are identical in shape. The zero torque and zero angle point on the solid line represents the heel strike of the stance phase. Arrow I is the plantar flexion of the foot from heel strike to foot flat (See lower panel of FIG. 13 for foot positions at each stage of a gait cycle). Arrow II represents the dorsiflexion movement of the foot from foot flat to mid-stance along the same angles as arrow I, but following a different torque profile. Arrow III represents the controlled dorsiflexion throughout the stance phase from mid-stance till heel off. Arrow IV represents the plantar flexion movement of the foot between heel off till toe off, where the swing phase of the prosthetic foot starts. Switching between torque-angle curves (e.g., using a cam-based transmission) is provided by multiple cam profiles. The shape of the cam profile determines the deflection of the energy storing element (e.g., leaf spring) during rotation of the ankle joint. As the ankle joint rotates, the spring is deflected by the cam-follower mechanism, and the shape of the cam profile determines the mechanics of the ankle joint. The cam profile is determined mathematically, enabling arbitrary ankle joint mechanics to be achieved.

The devices described herein are able to vary the average stiffness of the ankle joint by moving a repositionable sliding support beneath the spring (denoted pivot point in FIG. 2). The sliding support can be moved using a small motor in the distal end of the prosthesis. The foot only changes stiffness (or repositions the slider) when no weight being born by the foot, which occurs each step during the swing phase of gait (when the foot is in the air).

In some embodiments, a multiple (e.g., dual) cam profile provides or enhances energy recycling or variations in energy return rate and provides additional benefits by using multiple cam profiles. In some embodiments, one cam path stores energy in the initial part of the stance phase of walking, and saves this energy until the push off region, when it is then returned using a second or further cam profile, having the most benefit. This idea is generally depicted in FIG. 13. As shown in FIG. 13, the combination of the two curves leads to a dual-path cam which is depicted as the furthest right of the figure. The order that the cam profiles are engaged throughout the gait cycle is important to providing the recycling of energy. Since the mechanism is passive (no net-positive energy) the areas inside the torque-angle loops are equivalent.

The present disclosure contemplates any number of configurations for cams comprising multiple cam profiles or paths. The present disclosure is not limited to a particular configuration for switching between distinct cam profiles. Specifically contemplated are embodiments where one or more of the cam or cam follower components move relative to the other in order to switch the follower between multiple distinct cam profiles. Exemplary cams comprising dual cam profiles are described below and in FIGS. 14-19.

Figure 14A:
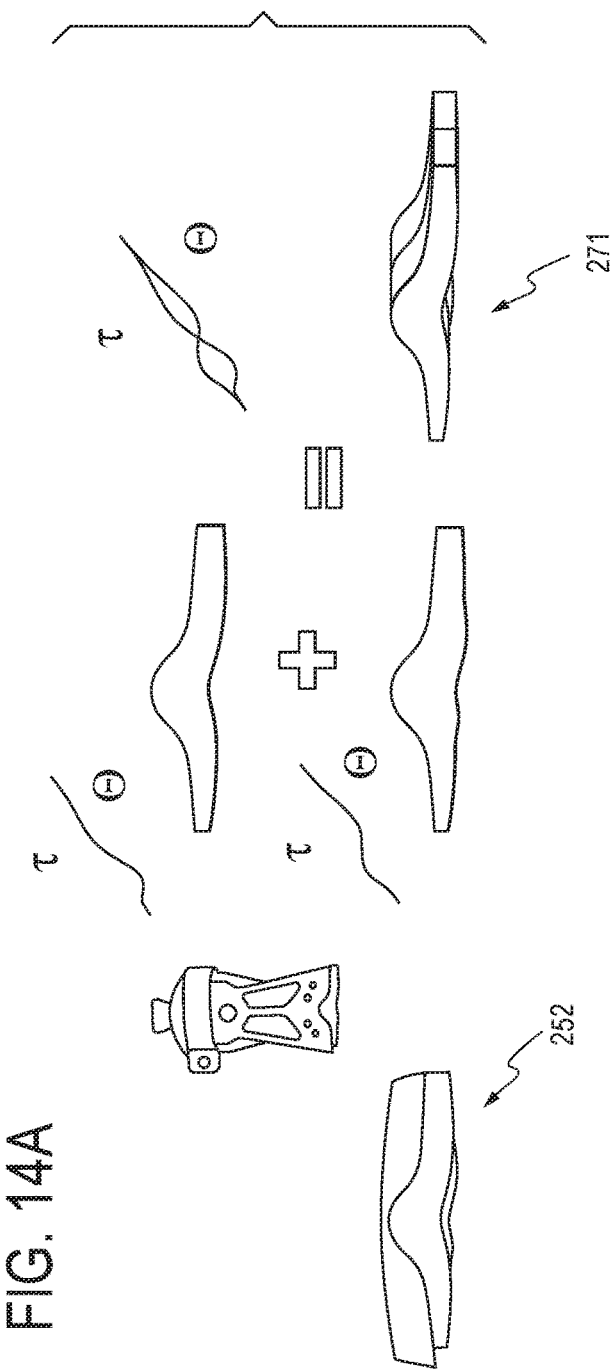
FIG. 14A displays torque angle profiles for a cam having two distinct cam profiles.
Figure 14B:
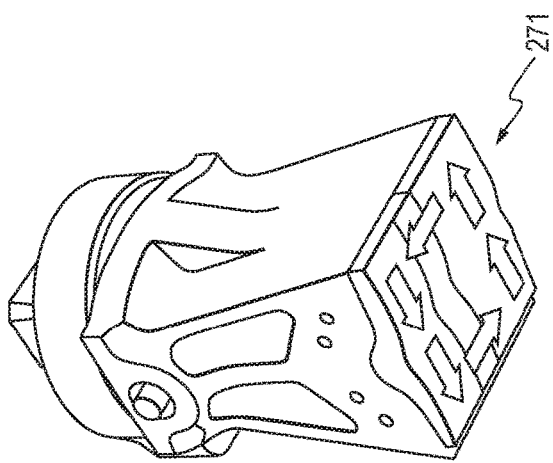
FIG. 14B displays a follower path across the two cam profiles of FIG. 14A.

FIGS. 14-15 display a dual cam profile embodiment where the cam follower switches between multiple cam profiles. Now referring to FIGS. 14A-B, shown are exemplary torque angle profiles for a dual cam profile. The left panel of FIG. 14A shows a view of an exemplary cam profile 252. The right panel shows torque angle curves for a dual cam profile 271. The right panel of FIG. 14A demonstrates how two distinct adjacent cam profiles form a dual cam path with different torque angle curves as described in detail in FIG. 13.

FIG. 14B displays a perspective view of a dual cam profile 271 located on the bottom surface of a cam. The arrows show the direction of movement of a cam follower during a gait cycle. The cam follower (not shown) transitions from a first cam profile to the adjacent, distinct cam profile at the positions shown by the arrows. The distinct cam profiles, as shown in FIG. 14A, form distinct torque-angle curves.

Figure 15A:
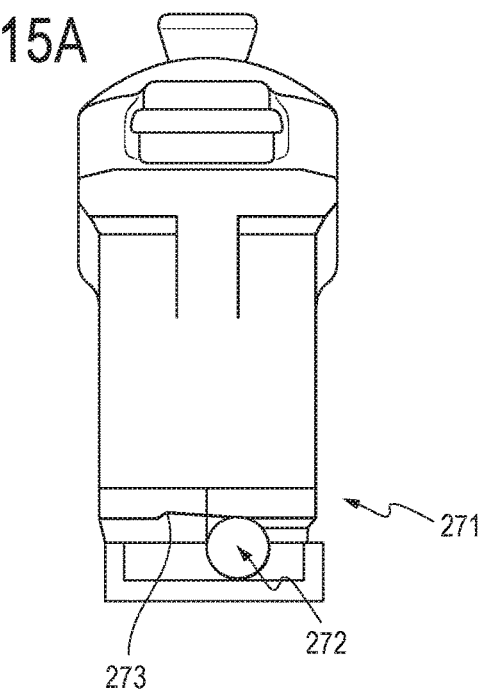
FIG. 15A displays a perspective view of a cam having exemplary dual cam profile.

FIGS. 15A-D display details of exemplary dual cam profiles where the cam follower moves relative to the cam profile. FIG. 15A shows an overview of a cam comprising dual cam profile 271 and slope 273. Also shown is spherical follower 272 in contact with dual cam profile 271. The slope 273 between the dual cam profiles 271 serves to guide the cam follower 272 from one cam profile to the other. Because pressure is applied on both sides of the follower, the slope 273 transitions the follower from one profile to the other.

Figure 15B:
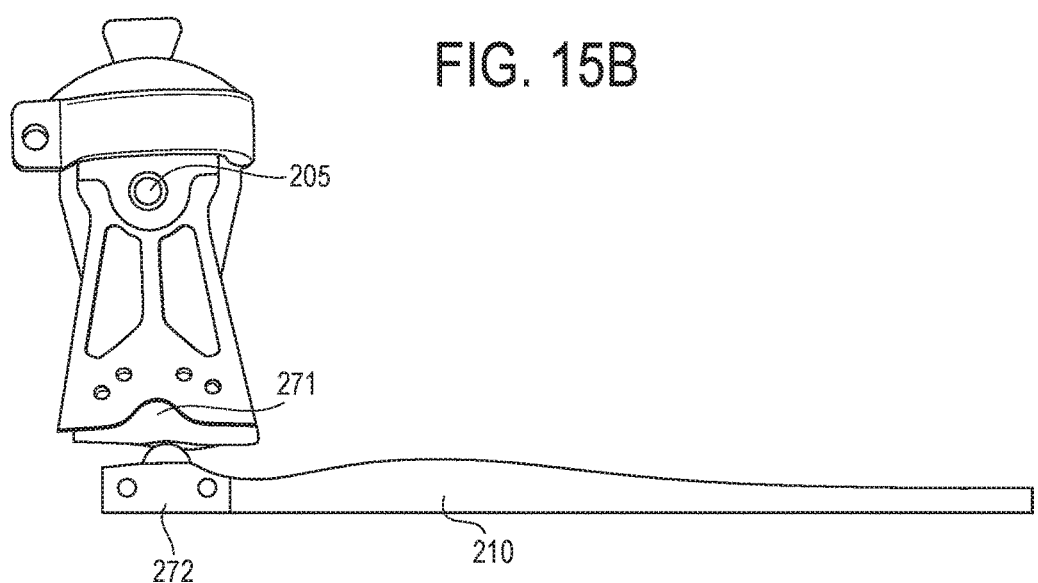
FIG. 15B displays a side view of one example of a cam having an exemplary dual cam profile integrated into a prosthesis.

FIG. 15B displays an overview of the dual cam profile 271 integrated into a device (e.g., ankle joint of a prosthetic foot). FIG. 15B shows dual cam profile 271 in operable communication with spring 210 and spherical cam follower 272. As the cam follower moves along one or both cam profiles of the dual cam profile 271, the spring is deflected.

Figure 15C:
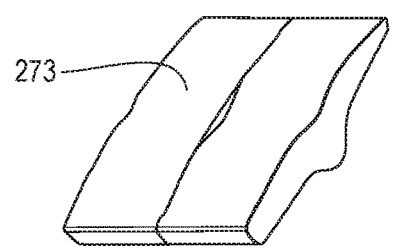
FIG. 15C displays a slope for a cam having a dual cam profile.

FIG. 15C displays a detailed view of dual cam profile 271 showing slope 273 and circular grooves 274. The grooves 274, which are machined in the cam profiles, aid in keeping the follower 272 in place, and guide it along the cam profile 271 during gait.

Figure 15D:
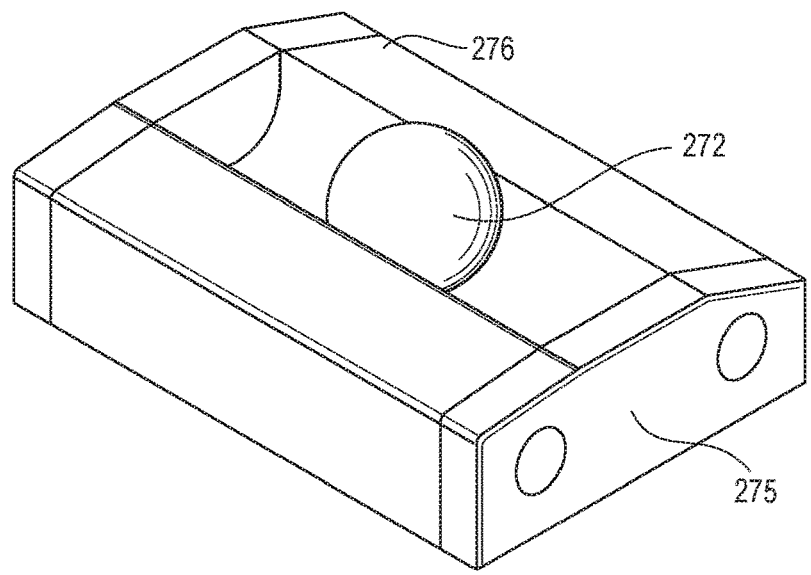
FIG. 15D displays spherical follower and housing.

FIG. 15D displays a detail view of the spherical follower 271 in a housing 276. In some embodiments, the housing further comprises a cap 275. The housing aids in mediolateral translation of the spherical following 272 between distinct cam profiles during gait.

In operation, in order to switch between the multiple cam profiles, a cam and follower transmission is utilized. Referring to FIGS. 15A-D, in some embodiments, spherical follower 272 rolls along the cam profiles 271, but also transitions between the cam profiles. The extremities of the dual cam-profile 271 allow for a transition between the separate cam profiles.

FIGS. 16-19 display an exemplary dual cam profile embodiment where the cam comprises a moving component and the cam follower is stationary. Referring to FIGS. 16A-C, shown is an overview of a cam with a dual cam profile comprising a moving component. FIG. 16A displays a perspective view of a cam profile 252 comprising a cam profile slider 279 and stationary component 281. The cam profile slider 279 comprises at least two distinct cam profiles 277 and 278 with different torque angle curves. The cam profile slider 279 moves relative to the stationary component 281 in order to switch the cam follower (not shown) between the distinct cam profiles 277 and 278.

Figure 16A:
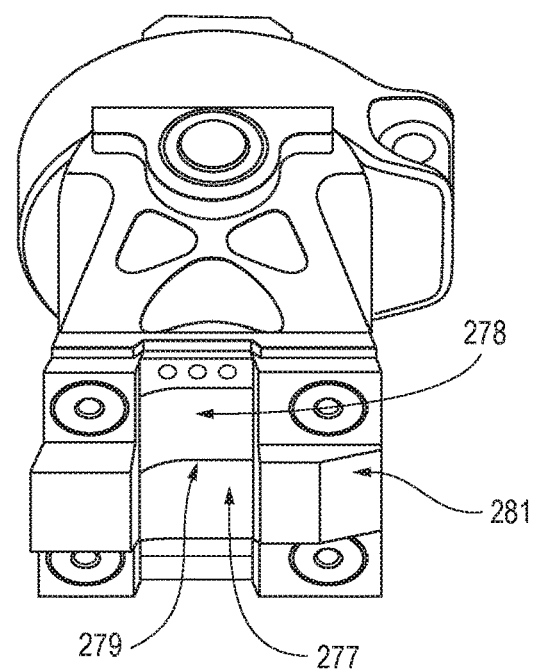
FIG. 16A displays a perspective view of an exemplary cam comprising a dual cam profile.
Figure 16B:
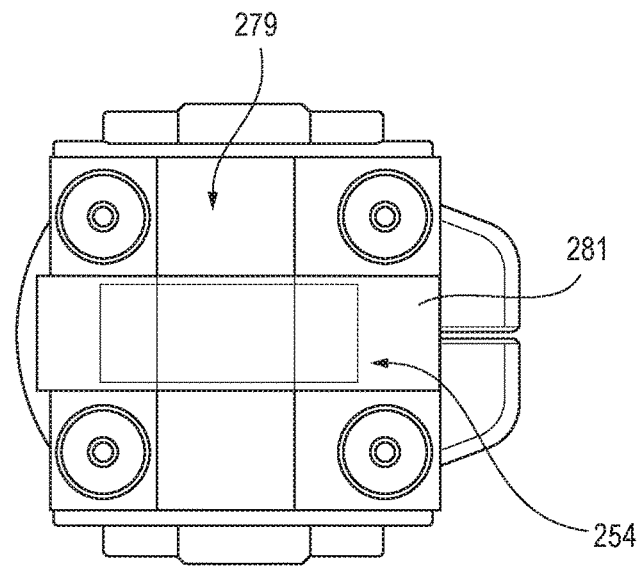
FIG. 16B displays a bottom view of an exemplary cam having a dual cam profile.

FIG. 16B displays a bottom view of the dual cam profile of FIG. 16A. Shown is cam profile slider 279, stationary component 281, and cam follower 254. When the cam profile slider 279 moves, the cam follower 254 remains stationary as it switches between cam profiles 277 and 278.

Figure 16C:
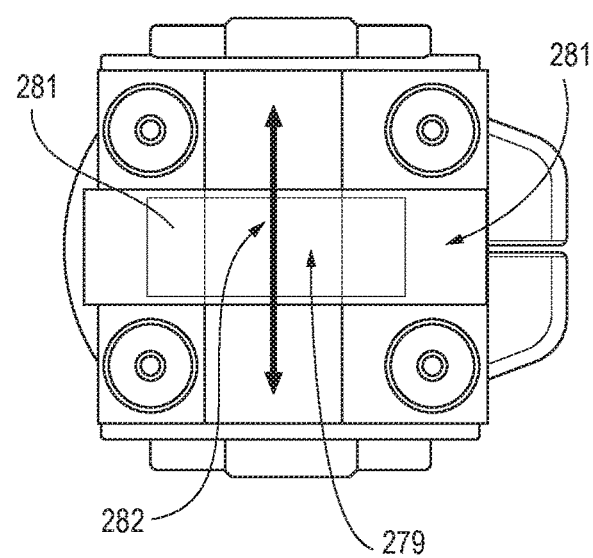
FIG. 16C displays a bottom view of an exemplary cam having dual cam profile.

FIG. 16C displays an additional bottom view of the dual cam profile of FIG. 16A. Shown is cam profile slider 279 and stationary component 281. The arrow 282 illustrates the direction of movement of cam profile slider 279 relative to the stationary component 281 and cam follower.

FIGS. 17A-D display detailed drawings of the dual cam profile of FIGS. 16A-C.

Figure 17A:
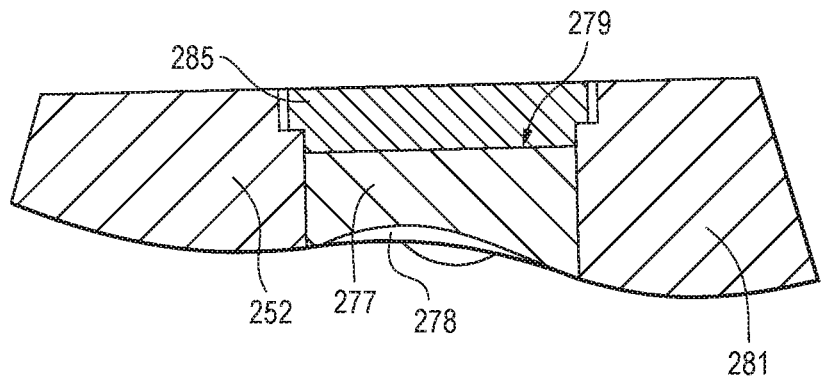
FIG. 17A displays a cross section of an exemplary cam having a dual cam profile.

Now referring to FIG. 17A, shows is a side cut-out view of cam profile 252 comprising cam profile slider 279 with dual cam profiles 277 and 278 and stationary component 281. As shown in FIG. 17A, in some embodiments, cam profile slider 279 comprises a top surface 285 and a bottom surface comprising cam profiles 277 and 278. In some embodiments, the top surface is constructed of a different material in order to decrease mass or friction. In some embodiments, the use of different materials for the top and bottom surfaces of the cam slider further decreases the difficulty of post-machining parts due to tolerancing issues.

Figure 17B:
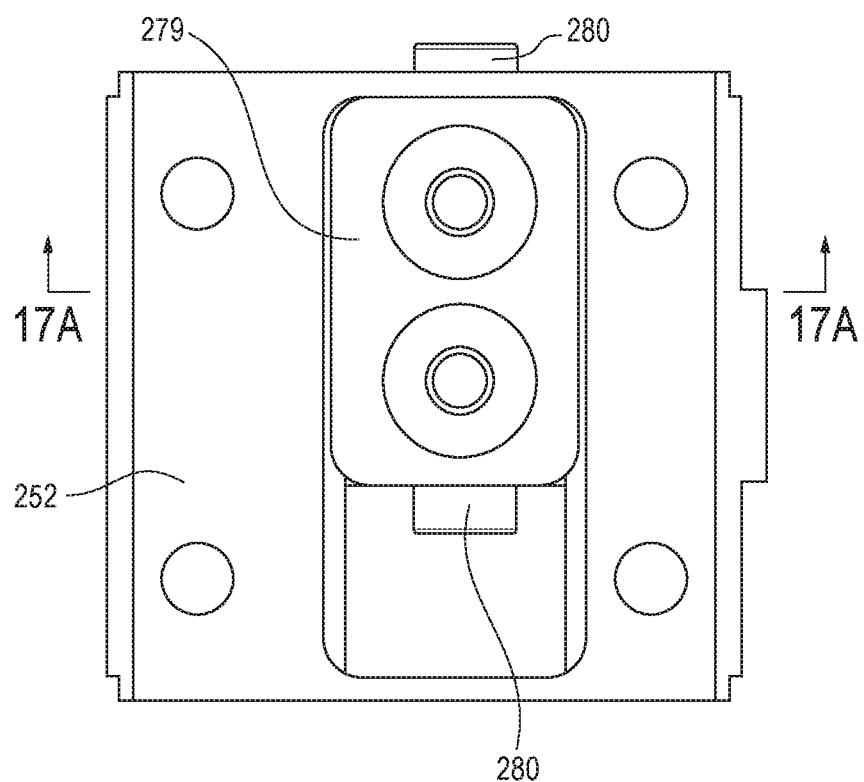
FIG. 17B displays a bottom view of an exemplary cam having a dual cam profile.

FIG. 17B displays a bottom view of cam profile 252, cam slider 279, and cam slider transport component 280. The cam slider transport component moves the cam profile slider 279 relative to the cam follower (not shown) in order to switch the cam follower between distinct cam profiles 277 and 278.

In FIG. 17B, the cam slider transport component 280 is shown as a pair of magnets. However, the present disclosure is not limited to a particular cam profile transport component 280. Examples of cam slider transport components include, but are not limited to, magnets (e.g., one or more pairs of magnets), solenoids, pneumatics, or linkage mechanisms.

Figure 17C:
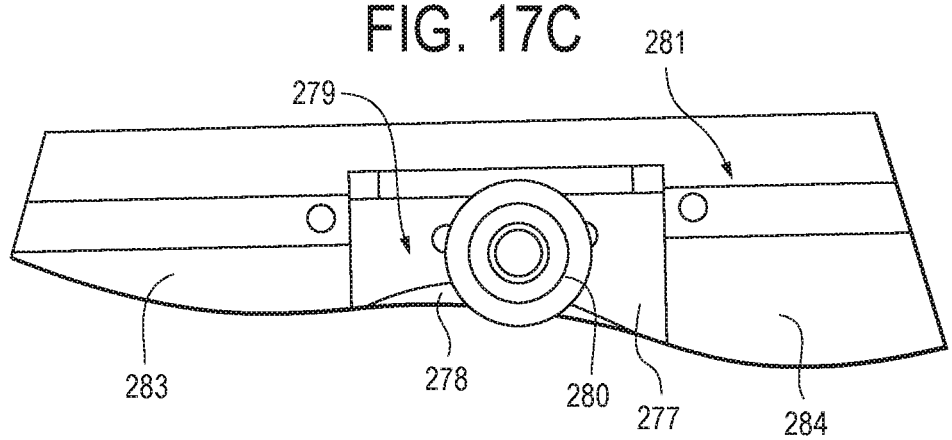
FIG. 17C displays a side view of an exemplary cam having a dual cam profile.

FIG. 17C displays a side view of cam profile slider 279 with distinct cam profiles 277 and 278. Also shown are cam profile transition zones 283 and 284. In use, the cam follower 254 (not shown) switches between distinct cam profiles 277 and 278. This switch occurs when the line contact between the cam follower and cam profiles 277 and 278 is in the transition zones 283 and 284. The transition zones 283 and 284 represent the point on the torque-angle plane where both torque-angle curves are identical in shape. This also results in the cam profiles having identical shapes (at this point). If the cam follower is in contact with the transition zones 283 and 284, cam profiles 277 and 278 are no longer loaded by the cam follower 254 and the switch between cam profiles 277 and 278 occurs in a passive or an active manner (e.g., with cam slider transport component 280).

Figure 17D:
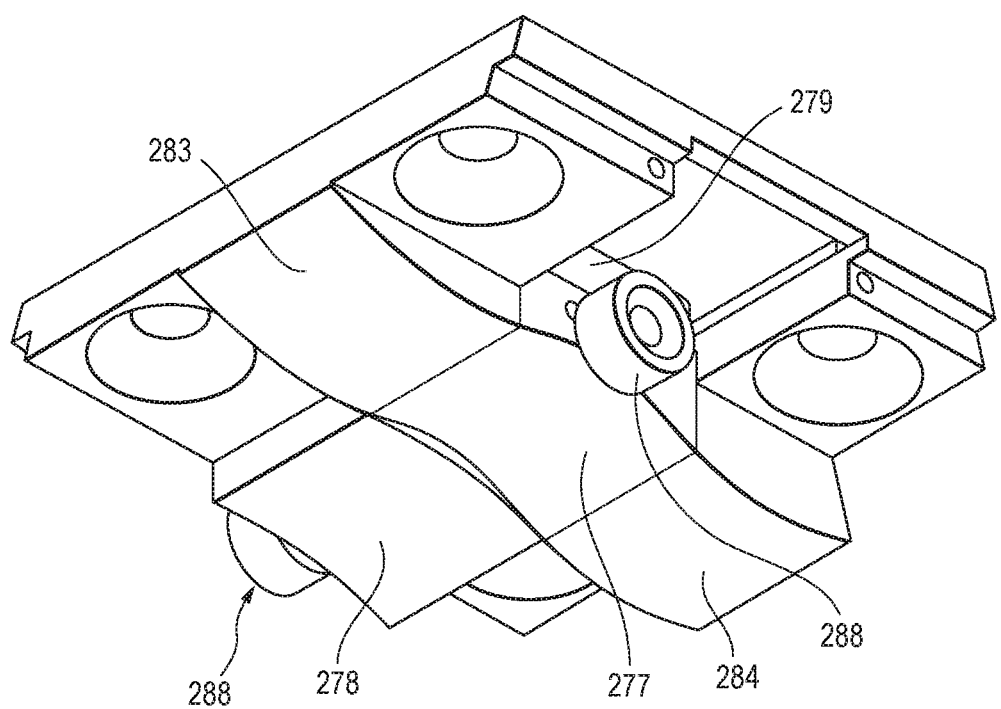
FIG. 17D displays a bottom view of an exemplary cam having a dual cam profile.

FIG. 17D displays an embodiment of the present disclosure where the cam slider transport component 280 is illustrated as a pair of slider magnets 288. When the cam follower is in contact with the transition zones 283 and 284, the cam profile slider 279 slides in the medio-lateral direction due to the magnetic force of the slider magnets 288. The magnet placement is such that at maximum plantar flexion the cam profiles switch from cam profile 277 to cam profile 278 (also represented by a switch from the solid line torque-angle curve to the striped line torque-angle curve as displayed in FIG. 13). This is because the north poles of the slider magnets 288 repel each other and the north pole and south pole of the slider magnets 288 attract each other. The magnet placement in the frame is reversed at maximum dorsiflexion to ensure a switch from cam profile 278 to cam profile 277 (e.g., striped line torque-angle curve to the solid line torque-angle curve from FIG. 13). The switching of cam profiles using magnets is further illustrated in FIGS. 18A-B described below.

Figure 18B:
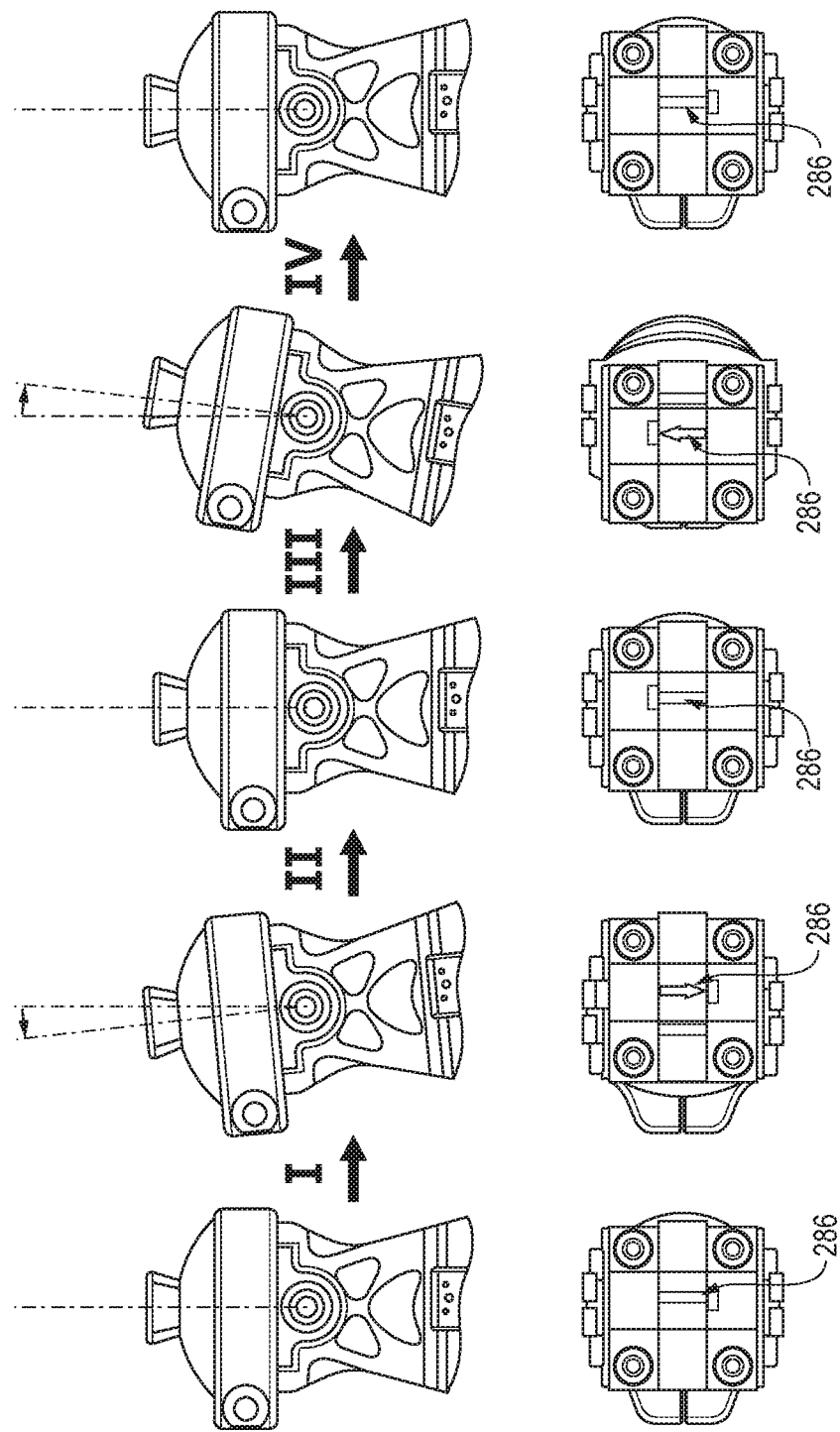
FIG. 18B displays cam profile switching during a step.

FIGS. 18A-B display an illustration of the switching between distinct cam profiles 277 and 278 during a gait cycle. Now referring to FIG. 18A, the left panel shows a cam with dual cam profiles. The transition zones 283 and 284 and cam profile slider 279 are labeled. Arrows show the direction of rotation of the cam around a center point during planter flexion and dorsiflexion. The middle panel of FIG. 18A shows a bottom view of the cam illustrating the positioning of a cam profile transport component comprising a plurality of slider magnets 288. The slider magnets 288 are adjacent the cam slider 279 and cam profiles 277 and 278. Also shown in FIG. 18A are two pairs of frame magnets 287. As shown in the middle panel of FIG. 18A, the frame magnets 287 are placed in pairs next to a magnet of opposite polarity in order to force the slider magnets to move the cam profile slider 279. In use, a slider magnet 288 and a frame magnet 287 become face to face (e.g., North to North pole), which causes a transition force to be applied to switch the profiles. In addition, as the cam profiles (or follower) are moving another frame magnet 287 on the opposite side begins to attract, pulling the assembly the rest of the way. The labelled line 286 in the center and right panel of FIG. 18 represents the line of the cam follower contact with cam profile.

FIG. 18B displays the flexion around the cam follower and position of the cam profile slider 279 during a single gait cycle. The top panel of FIG. 18B depicts the orientation of the cam profiles, relative to the neutral angle, throughout the gait cycle. The numbering refers to the gait phases displayed in FIG. 13. The bottom panel of FIG. 18B shows the medio-lateral switch of the cam profiles. Transitioning between the two cam profiles, and thus the two torque angle curves, occurs when the cam follower line contact is in the transition zone (labeled in FIG. 18A). At that time, the cam profile slider is under a no-load condition from the cam follower and able to slide freely in the medio-lateral direction due to the magnetic forces acting on the sliding part. This switch occurs twice every stance phase, once when the transitioning plantar flexion angle is reached and once when the transitioning dorsiflexion angle is reached. For example, still referring to FIG. 18B, the left panel (1) represents the cam follower line of contact 286 at the beginning of a gait cycle. The next panel (11) represent the direction (via the arrow) of the cam profile slider during plantar flexion along the line of contact 286. The frame magnets 287 act on the cam profile slider and slider magnets 288 to move the cam profile slider. The next panel (111) represents mid gait. The following panel (IV) represents the direction of the cam profile slider (via the arrow) during dorsiflexion along the line of contact 286 due to magnetic forces of frame magnets 287. The right panel (V) represents the return of the cam profile slider to the original position.

Figure 19A:
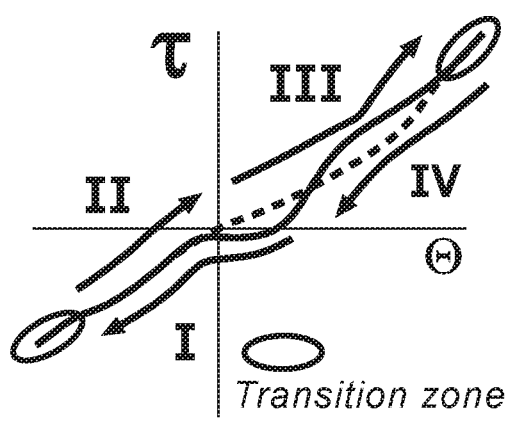
FIG. 19 displays exemplary energy curves for cams having dual cam profiles described herein.

Energy recycling is one of the benefits of decoupling the energy storage and return by means of a dual cam-based transmission. Other applications of this mechanism in passive prosthetic feet are illustrated in FIGS. 19A-D. Referring to FIG. 19A, shown is torque-angle curve of an alternative configuration where the neutral angle of the solid line torque-angle curve is modified to a dorsiflexed position. This prevents toe scuffing as the foot is dorsiflexed throughout the swing phase. The two curves differ slightly in the mid- to late stance to compensate for the energy difference due to the difference in neutral ankle angles.

Figure 19B:
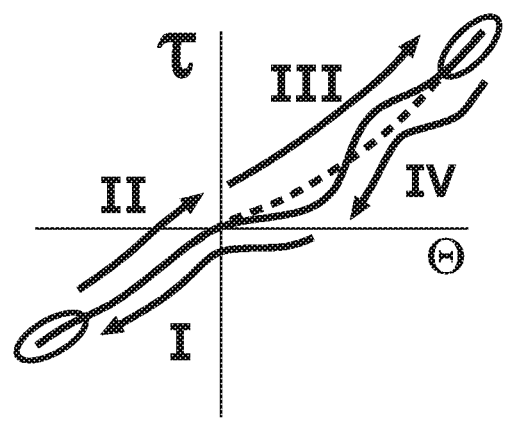

FIG. 19B displays a torque-angle curve of an alternative configuration where there is a difference in the rate and/or timing at which energy is stored and released. By applying this concept, information is gained about whether the optimal rate of energy storage and return are equal in passive prostheses or not.

Figure 19C:
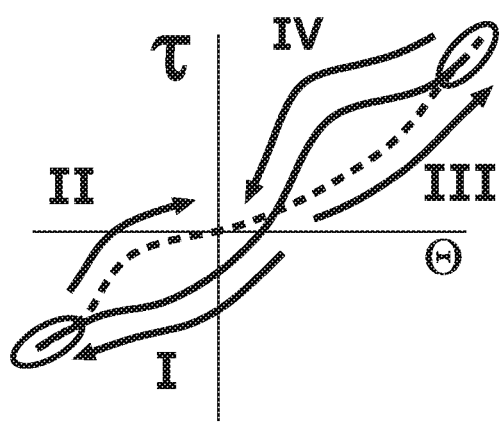

FIG. 19C displays a torque-angle curve of an alternative configuration using the energy recycling configuration from FIG. 13 and the dorsiflexed neutral angle from FIG. 19A. By combining the two embodiments, foot clearance is achieved during the swing phase and the range of motion for capturing energy is increased.

Figure 19D:
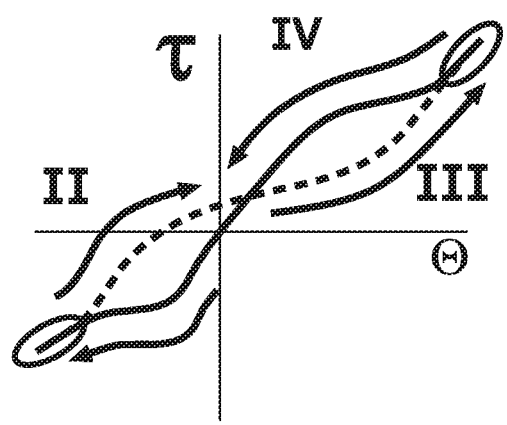

FIG. 19D displays a torque-angle curve of an alternative configuration using the energy recycling configuration shown in FIG. 13 and a change of the neutral angle of the striped line (e.g., by providing plantarflexion during the stance phase) This increase the range of motion throughout which energy can be captured and an improvement in energy storage.

Leaf Spring. To vary stiffness, the support condition of the leaf spring 210 can be actively varied continuously throughout the length of the leaf spring 210. The leaf spring 210 may be coupled to a clamp support 270 anteriorly towards the toe 274, and a slider 220 in the mid-foot region. A lead screw 232 positions the slider 220 along a range of motion so that the position of the slider 220 is adjustable along the bottom surface of the leaf spring 210, as shown in FIG. 2B. In an example, the lead screw may be a 6.35 mm diameter, non-backdriveable lead screw capable of dynamic loads up to 700 N, with 1.27 mm lead (Nook Industries, Cleveland, Ohio, USA), which is able to position the slider 220 along an 85 mm range of motion. A DC motor 230 powers the lead screw 232. In an example, the DC motor 230 is a 10 Watt brushed DC Motor (Maxon Motors, Switzerland) with a 3.9:1 planetary gearhead and capable of 25 mNm intermittently. The DC motor 230 also may have an integrated 1024 counts-per-revolution incremental encoder 260, which may be used for positioning of the DC motor 230.

The leaf spring 210 may be constructed from unilateral fiberglass (Gordon Composites, CO, USA). Fiberglass can be a useful material in this application because of its high energy-storing capacity, making it up to eight times lighter and smaller than an equivalent spring made of steel. The leaf spring 210 may be shaped for roughly equal stresses on the outer strands at the primary slider position. In a preferred example, the height of the leaf spring 210 varies, as shown in FIG. 2B, resulting in lower shear stresses and making it less likely for delamination to occur. In other examples, the width of the leaf spring 210 may be varied rather than or in addition to varying the height of the leaf spring 210.

The rotational stiffness of the leaf spring 210 can be derived from experimental results of translational spring stiffness, shown in FIG. 4, and the effective moment arm. To predict ankle stiffness curves at different leaf spring stiffnesses, which are generated by different slider positions, a forward model may be employed that reverses through the presented equations. The translational stiffness of the spring, position of the virtual spring pivot, and spring preload are adjusted to simulate movement of the slider.

The translational stiffness of the leaf spring as a function of slider position may be found using a material testing system, such as Sintech 20G (Singapore, Singapore). Over an order of magnitude of translational stiffness modulation may be possible within the slider's range of motion, for example, 0.17-2.8 kN/mm.

Figure 9:
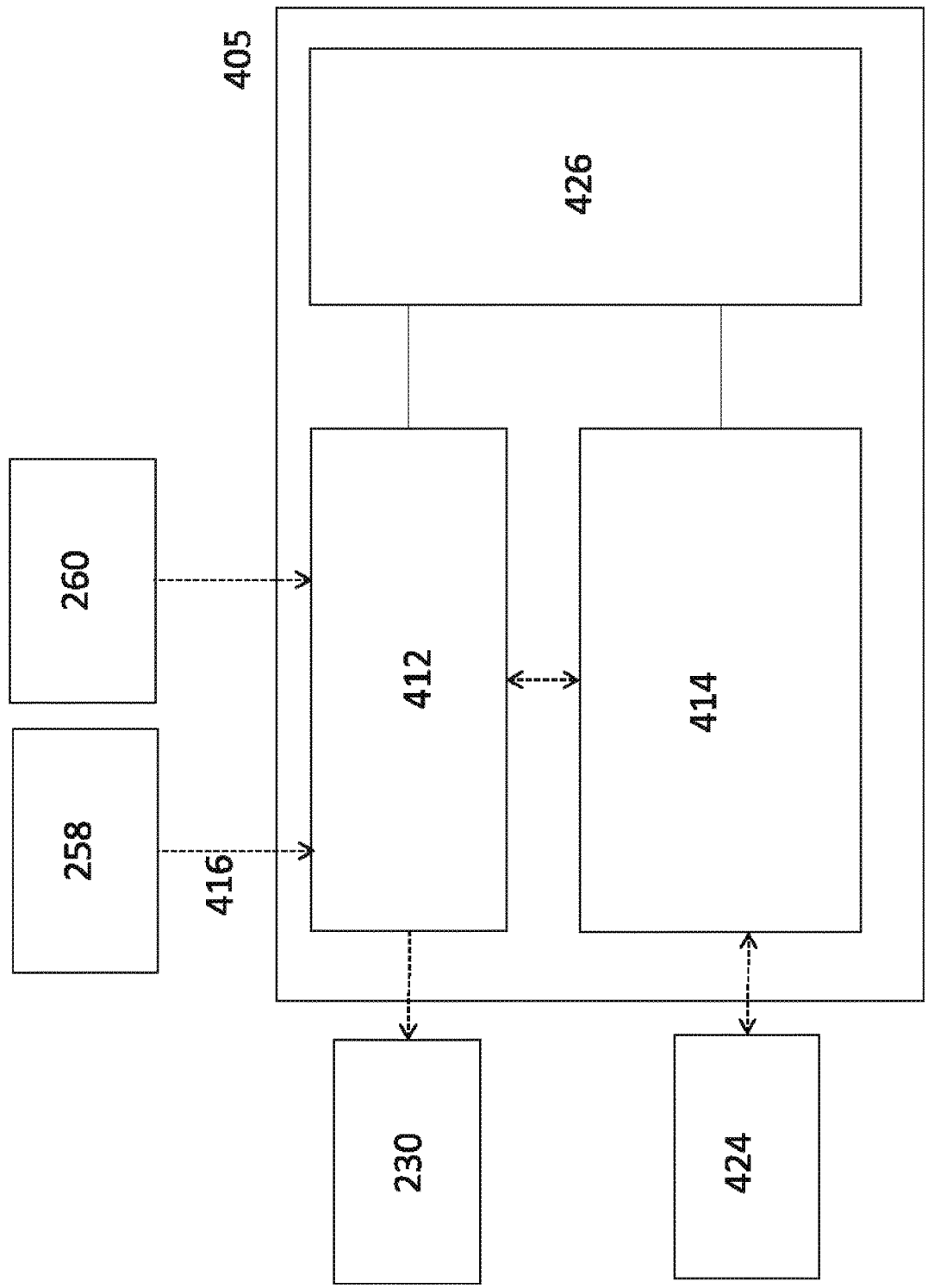
FIG. 9 displays a pictoral representation of a system for controlling an ankle prosthesis.

Mechatronics. FIG. 9 displays a representation of an exemplary mechatronic system used to power and control the electrical components of the prosthesis 201. The low-level positioning of the DC motor 230 may be performed by a motor controller 412, such as an EPOS2 motor controller (Maxon Motors, Switzerland). A computer 414, which may be a single board computer such as a Linux computer (Raspberry Pi Zero, Raspberry Pi Foundation, Cambridge, UK) sends desired position to the motor controller 412, for instance by a step-direction method. In a step-direction method, each pulse is scaled to move the slider 220 by a predetermined amount, such as 1 mm, which provides sufficient resolution for stiffness modulation. For example, the motor controller 412 may cause the motor encoder 260 to drive the DC motor 230 an appropriate amount to turn the lead screw 232, which moves the slider 220 the 1 mm length in the intended direction along the lead screw 232. The computer 414 also can read ankle position, measured by an encoder 258, such as a 14-bit absolute encoder (AS5048A AMS, Premstaetten, Austria), via an interface 416 such as a Serial Peripheral Interface. Stiffness modulation may be prevented when the ankle joint 205 is outside of a predetermined limit, such as ±1° of neutral, as measured by the encoder 258. When the ankle joint 205 is outside such a range, that indicates that the spring 210 is compressed beyond the preload, and movement of the slider 220 is not possible with the available torque provided by the DC motor 230. The computer 414 can communicates with a host computer 424 over known communication protocols, such as Wi-Fi. A battery 426, such as a 14.8 V, 430 mA-hour Lithium-Polymer battery (Venom, Rashdrum, ID, USA) powers the motor controller 412, the computer 414, any associated electronics, and the DC motor 230. The computer 414, motor controller 412, and battery 426 may be housed in an electronics box 405, which can be mounted to the prosthesis socket, making the design entirely mobile for non-tethered operation.

To alter mechanics during swing phase, the slider 220 needs to reposition quickly. The reference position may be modified by the computer 414, which sends the appropriate command to the low-level motor controller 412 via the step-direction method. Step responses from the highest stiffness (100%) to several stiffnesses are shown in FIG. 5. Specifically, FIG. 5 depicts a graph plotting step responses from standing stiffness (100%) to other stiffnesses. The dashed line in FIG. 5 denotes the step response to the slider position of the primary stiffness (47%). The maximum speed of the slider is 80 mm/s, and is limited by the motor and gearhead's maximum permissible speed. Desired position, actual position, and current were recorded by the EPOS2 Studio software (Maxon Motors, Switzerland).

Frame. In addition to impact forces and the weight of the person using the prosthesis 201, there can be large forces in the frame 262 from the high loads on the leaf spring 210. The frame 262 may therefore be constructed from a material of high strength, high stiffness, and low weight, such as 7075-T6 Aluminum. The ankle joint 205 may have mechanical hard stops, for instance at 300 of plantarflexion and 30° dorsiflexion. Angular contact bearings can support a cam profile 252. The prosthesis 201 may be attached to a socket worn by an amputee via an adaptor 256, such as a titanium pyramid adaptor with rotational adjustability (Bulldog Tools, Inc., Lewisburg, Ohio, USA).

Figure 8:
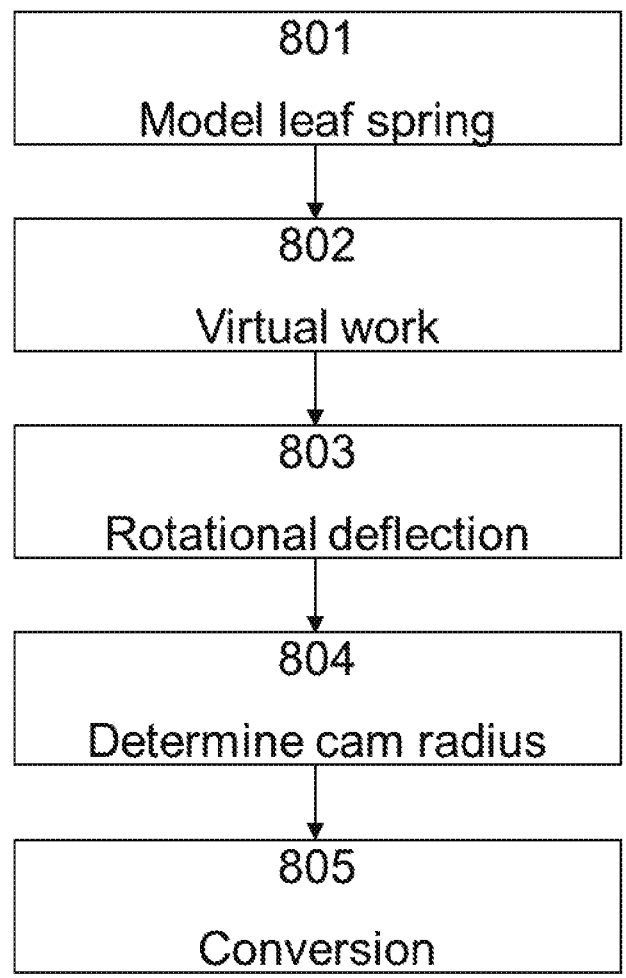
FIG. 8 displays a representational diagram for a method of deriving a cam profile.

Cam Design—Mathematical Modeling. In order to obtain the primary stiffness curve for the ankle prosthesis 201, an appropriate cam profile 252 may be designed. A summary of an exemplary strategy for derivation of a cam profile 252 can be summarized as follows, and is shown in FIG. 8. In 801, the leaf spring 210 may be modeled as a rotary spring centered at a simple support. In 802, the problem may be framed using the principle of virtual work, where the energy stored in the ankle prosthesis 201 is equal to the energy stored in the spring. In 803, solve for rotational deflection of the spring. In 804, use the geometry to determine cam radius from ankle angle and spring angle. In 805, convert from ankle space to cam coordinates.

Figure 3A:
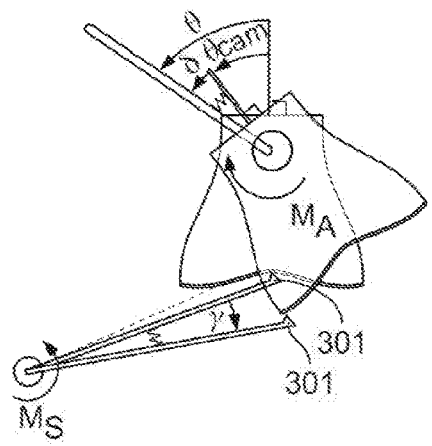
FIG. 3A displays a first diagram of a mathematical description of a cam profile and a cam follower.
Figure 3B:
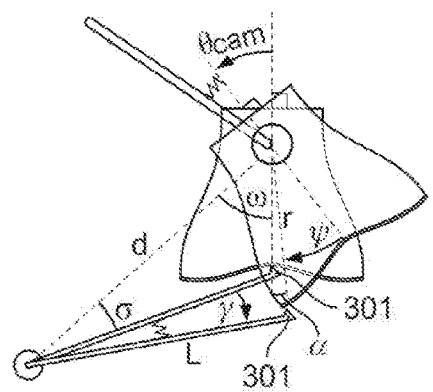
FIG. 3B displays a second diagram of a mathematical description of a cam profile and a cam follower.

FIG. 3A and FIG. 3B display diagrams that reflect a mathematical description of the cam profile and the cam follower. The cam follower is simplified to a point (indicated by the triangle 301). Downward deflection of the cam follower ($\gamma$) is resisted by the leaf spring (Ms), which has a 'virtual pivot' located at the simple support/slider, and is considered a rotational spring. Deflection of the ankle ($\theta$) causes a moment at the ankle ($M_A$), produced by the force between the cam follower and cam profile. The leaf spring is preloaded a small angle $\gamma 0$ (the unpreloaded position is shown). FIG. 3B reflects the geometry used to find the cam profile in polar coordinates (r, $\psi$) from $\theta$ and $\gamma$. The variables d and $\sigma$ (sigma) are known constants related to the geometry of the ankle prosthesis. The problem can be simplified in that the cam follower may be modeled as a point, as mentioned above. The final cam profile may require a perpendicular offset equal to the radius of the cam follower.

It cannot be assumed that a spring such as a fiberglass leaf spring behaves like a linear, translational spring. In the example of the prosthesis 201 shown in FIGS. 2A and 2B, the cam follower 254 is attached above the neutral plane of the spring 210, so the horizontal component of the force on the cam 250 creates a moment on the spring 210. Additionally, the cam follower 254 does not travel straight down as the leaf spring 210 deflects, but follows an arc about a virtual pivot. This virtual pivot point may be modeled as being at the simple support. Alternatively, a more accurate model of the virtual pivot point may be polycentric, dependent on the angle of the load, and somewhere between the simple support and the cam follower. Another source of series compliance is the flexure of the aluminum frame. Thus, without correction, the torque-angle curve may be less stiff than intended. Series compliance at the ankle joint may be modeled at the ankle joint, so that the moment on this compliance is equal to the moment on the ankle. The associated deflection is depicted in the figures as S. For example, the series compliance may be 1200 Nm/rad.

In an example, the cam profile may be determined by using a mathematical approach based on the principle of virtual work. The energy stored in the ankle joint is equal to the sum of the energy stored in the physical spring and the unwanted series stiffness, as reflected in Equation 1 below:

$$\int_0^\gamma M_S d\gamma = \int_0^\theta M_A d\theta - \int_0^\delta M_A d\delta. \tag{1}$$

The plantarflexion and dorsiflexion regions may be individually solved, so the lower limit of integration is at the equilibrium position. The ankle moment $M_A$ is defined as a function of $\theta$, and the series stiffness experiences the same moment, so its associated deflection is reflected in Equation 2 below:

$$\delta = \frac{M_A}{k_2}. \tag{2}$$

At the equilibrium position $\theta=0°$, the spring is preloaded a small angle $\gamma_0$. Equation 1 can be written as Equation 3, below:

$$\int_0^\gamma k(\gamma + \gamma_0) d\gamma = \int_0^\theta M_A d\theta - \int_0^\delta M_A d\delta. \tag{3}$$

In Equation 3, k is the stiffness of the leaf spring (as a rotary spring). The left side of this equation may be integrated to:

$$\frac{1}{2}k\gamma^2 + k\gamma_0\gamma + c = \int_0^\theta M_A d\theta - \int_0^\delta M_A d\delta. \tag{4}$$

where c, the constant of integration, can be found to equal zero from the initial conditions: $\theta=0$, $\gamma=0$, $\delta=0$. We then solve for $\gamma$ as a function of $\theta$ with the quadratic formula, so that $$\gamma(\theta) = -\gamma_0 + \sqrt{\gamma_0^2 + \frac{2}{k}\left(\int_0^\theta M_A d\theta - \int_0^\delta M_A d\delta\right)} \tag{5}$$

The integrals in Equation 5, which represent the work stored by the ankle and the series compliance, can be numerically solved, since we are specifying torque-angle relationship at the ankle. From $\gamma$, we can derive r, the radius of the cam profile at a given $\theta$, from the defined geometry (via law of cosines) as:

$$r(\theta) = \sqrt{l^2 + d^2 - 2ld\cos(\gamma + \sigma)} \tag{6}$$

where σ is the angle between the initial position of the spring and d, a line drawn between virtual spring centers. Since the cam follower does not travel only vertically (see FIGS. 3A and 3B), we need to find ψ, in order to have a polar representation of the cam profile as (ψ, r):

$$\psi(\theta) = \theta_{cam} - \alpha = \theta - \theta - \alpha \quad (7)$$

where α is the small angle between r and vertical, due to the leaf spring not deflecting straight downward. We can trigonometrically find α, using the geometry of the setup and the law of sines:

$$\alpha(\theta) = \sin^{-1}(L \sin(\sigma + \gamma(\theta))) + \omega \quad (8)$$

where d and y are respectively the diagonal and vertical distances between the ankle axis and virtual pivot of the spring, and σ is the angle between the line d and the initial position of the leaf spring. The numerical results, now in polar coordinates as (r, ψ) from Equations 6 and 7, are converted to Cartesian coordinates, and an offset curve corresponding to the final cam profile is created with a perpendicular offset of the cam follower radius.

Figure 12:
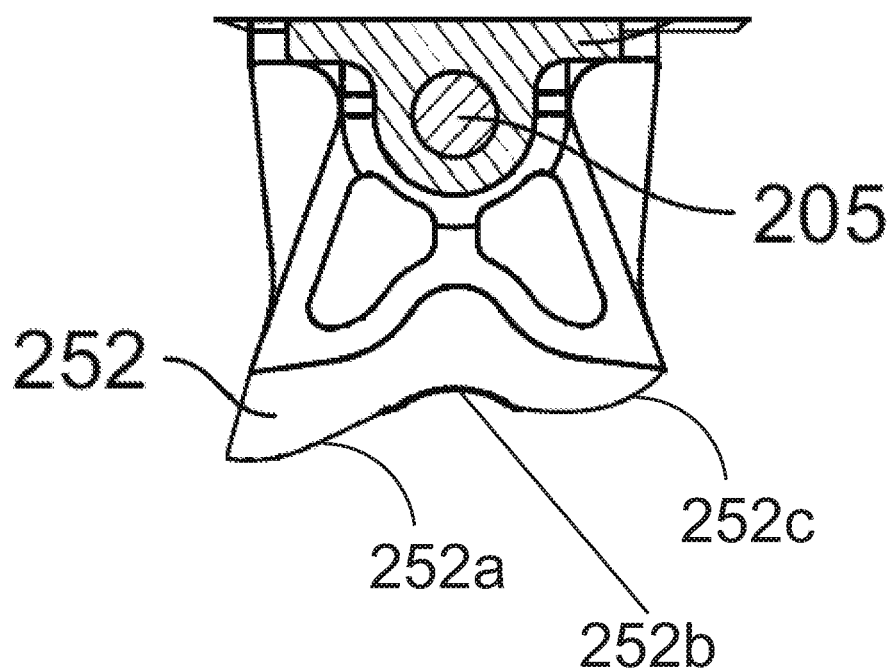
FIG. 12 displays a view of an exemplary cam profile with a curved outer edge.

FIG. 12 displays an enlarged view of an exemplary cam profile 252 with an outer edge that is shaped in accordance with the methods described above. The outer edge has a curved shape is comprised of a first portion 252a, a second portion 252b, and a third portion 252c. The first portion 252a is the portion against which a cam follower 254 rolls during plantarflexion of the prosthesis 201. The second portion 252b is the portion in which the cam follower 254 is positioned during equilibrium (for instance, as shown in FIG. 2B). The third portion 252c is the portion against which a cam follower 254 rolls during dorsiflexion of the prosthesis 201. As shown in FIG. 12, each section is curved, with second portion 252b having a concave shape with reference to a cam follower 254, and first portion 252a and third portion 252c each having a concave shape with reference to a cam follower 254.

Figure 6:
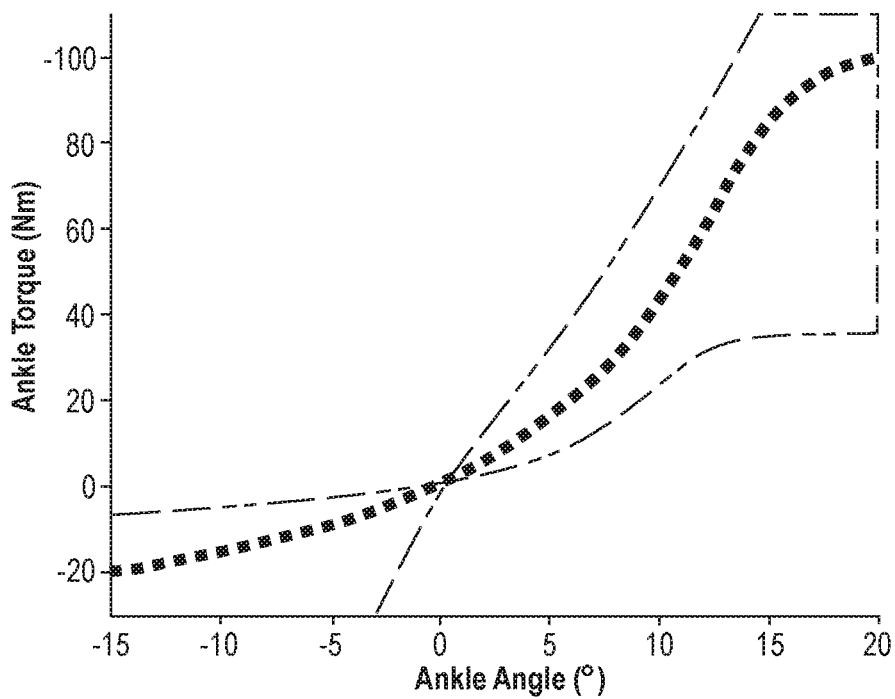
FIG. 6 displays a graph that plots a primary desired quasi-stiffness curve for walking, wherein the shaded region reflects the range of possible stiffnesses.

Choosing a cam profile. In an example, a cam profile 252 may be optimized for a 70 kg subject walking with the slider 220 positioned at 47% of the range of slider movement. According to the forward model, this position allowed an appropriate range of stiffnesses, higher and lower than what is needed for walking. The predicted range of stiffnesses and the desired primary stiffness curve for walking are plotted in FIG. 6. As shown in FIG. 6, a primary desired quasi-stiffness curve for walking is depicted in a dashed line, and the range of possible stiffnesses predicted for the range of positions of the slider 220 are indicated in the shaded are surrounding the dashed line.

Weight. In an example, the ankle, not including electronics, weighs 908 g. The electronics, which can be mounted more proximally on the prosthetic socket to reduce effects on the dynamics of leg swing, may weigh 170 g (including battery).

Stiffness Modulation. To minimize weight and size, the stiffness modulating mechanism was designed to only be utilized when no load is applied to the spring (other than a slight preload). FIG. 4A illustrates how moving the simple support towards the load increases spring stiffness. Experimental results of translational leaf spring stiffness is shown as a function of the slider position. Individual points in the graph in FIG. 4B represent tested positions. As shown in FIGS. 4A and 4B, as the slider position moves away from the beam support, the beam stiffness increases as shown, for example, in the graph shown in FIG. 4B.

The torque-angle relationship may be measured using a custom rotational dynamometer and the encoder 258 on the ankle joint 205. In an example, the dynamometer comprises a motor (BSM90N-3150AF, Baldor, Fort Smith, Ark.) and 6-axis load cell on the motor output (45E15A M63J, JR3, Inc., Woodland, Calif.). The ankle encoder may be sampled at 100 Hz by the onboard computer, and the load cell may be sampled at 1 kHz. The ankle may be fixed to a pyramid adapter on the dynamometer, and the ankle axis may be aligned with the axis of the dynamometer. The dynamometer can move the ankle at a constant speed in either plantarflexion or dorsiflexion up to and back from the peak angle over a period of eight seconds. The peak angle tested can be smaller at stiffer settings, so as not to overload the spring, cam follower, or frame. The test may be repeated at 10 slider positions across the slider's range of motion.

Figure 7:
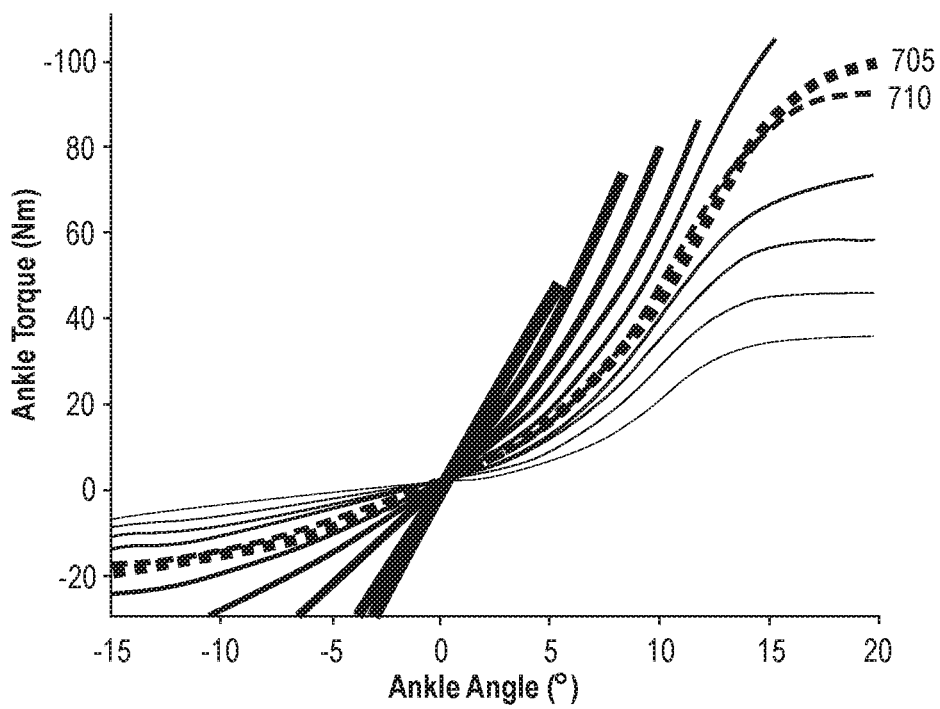
FIG. 7 displays a series of plots that experimentally characterize stiffness profiles of an exemplary ankle prosthesis at different stiffness profiles.

An experimental characterization of the stiffness profiles is shown in FIG. 7. The nine solid lines reflect testing on nine different slider positions across the range of motion of the slider 220. Dashed line 705 reflects the desired primary stiffness profile, which was designed for a slider position of 47%. Dashed line 710 reflects the experimentally determined profile at that slider position. Stiffness around 0° (measured as the average stiffness between −1° and 1°) at the highest stiffness level is 9.2 Nm/deg, and for the lowest stiffness level is 0.68 Nm/deg. Averaging across dorsiflexion trials, hysteresis resulted in a loss of only 1.9% of the energy stored.

The specific primary stiffness curve and primary slider position may be selected to balance several design features that may enhance clinical impact. A higher stiffness can improve standing stability, and a lower stiffness to improve range of motion during stair and ramp traversal. The selection of primary slider position governs how the stiffness profile can be varied from the primary stiffness profile. Thus, by selecting the primary slider position to be offset to either the anterior or posterior range of the spring, the available stiffness profiles can be shifted towards a more stiff or less stiff range, respectively. Thus, the primary stiffness profile and the selection of the primary slider position enables further customization of the mechanics, which may be altered depending on the design goals.

In an example, stiffness of the ankle can be modulated only during the swing phase of gait, or during static standing, when the ankle has negligible torque. By accepting this limitation, the sliding mechanism in the ankle can be built with no bearings or linear rails, because of the very low dynamic loads. The interface between the slider and frame may be comprised of two 1 mm thick pads of a high load thermoplastic, such as Delrin® (DuPoint USA, Wilmington, Del.), and the rolling contact with the spring rotates in high-load bushings. In particular, linear rails are significantly heavier, and the high static loads would prohibit the use of rails that could fit in the desired anatomical envelope. If the spring is compressed (by either a plantar- or dorsiflexion torque), friction between the roller and slider, or between the slider and Delrin pad, is too great for the motor to overcome.

Combining Intent Recognition. Adjusting ankle stiffness continuously during gait transitions may be achieved when using an intent recognition system, for instance, the kind described in U.S. Pat. No. 9,443,203 by Aaron Young and Levi Hargrove, titled Ambulation prediction controller for lower limb assistive device, incorporated herein by reference in its entirety. The computer 414 may execute the computer instructions used to recognize the intended ambulatory mode of the prosthesis 201, such as standing, walking, or traversing stairs. In other examples, a change in ambulation mode may be detected more simply, for instance using a decision table.

Advantages. The means of modulating stiffness described herein have several advantages. The range of stiffness profiles able to be implemented varies by an order of magnitude, due to the increasing rate of stiffness variation as the slider 220 moves posteriorly towards the heel 265. This nonlinearly increasing stiffness, coupled with the low inertia for slider 220, leads to a high stiffness modulation bandwidth. Additionally, by moving the slider 220 with a lead screw 232, which is non-backdriveable, the DC motor 230 is not required to maintain a holding torque, thus decreasing the electrical energy required for use of the prosthesis 201. Finally, the prosthesis 201 can be conveniently packaged in the anatomical envelope of the human foot-ankle complex, maintaining a cosmetic and low profile for amputees with longer residual limbs.

The simple mechanics of the prosthesis 201 improves robustness and avoids the more expensive actuation and transmission components that generally come with fully powered prostheses which add or dissipate energy. The prosthesis 201 is generally lighter than heavier fully powered prosthesis.

In another example, an ankle prosthesis is fully passive, thereby enabling the prosthesis to require no additional, outside power source or computing. This exemplary prosthesis may be made less expensively and may be used by a broader population. This example ankle prosthesis does not need to charge a battery. Additionally, it does not require an intent recognition algorithm that adjusts the ankle's mechanics automatically. The ankle prosthesis may have mechanics that are manually adjustable, for instance, by the user of the prosthesis. For example, the ankle prosthesis mechanics may be adjusted using a lever connected to a Bowden cable, which is a type of flexible cable used to transmit mechanical force by the movement of an inner cable relative to a hollow outer cable housing. This would allow the wearer to adjust the prosthesis mechanics to a setting (e.g. "stair setting") manually at will.

Figure 10:
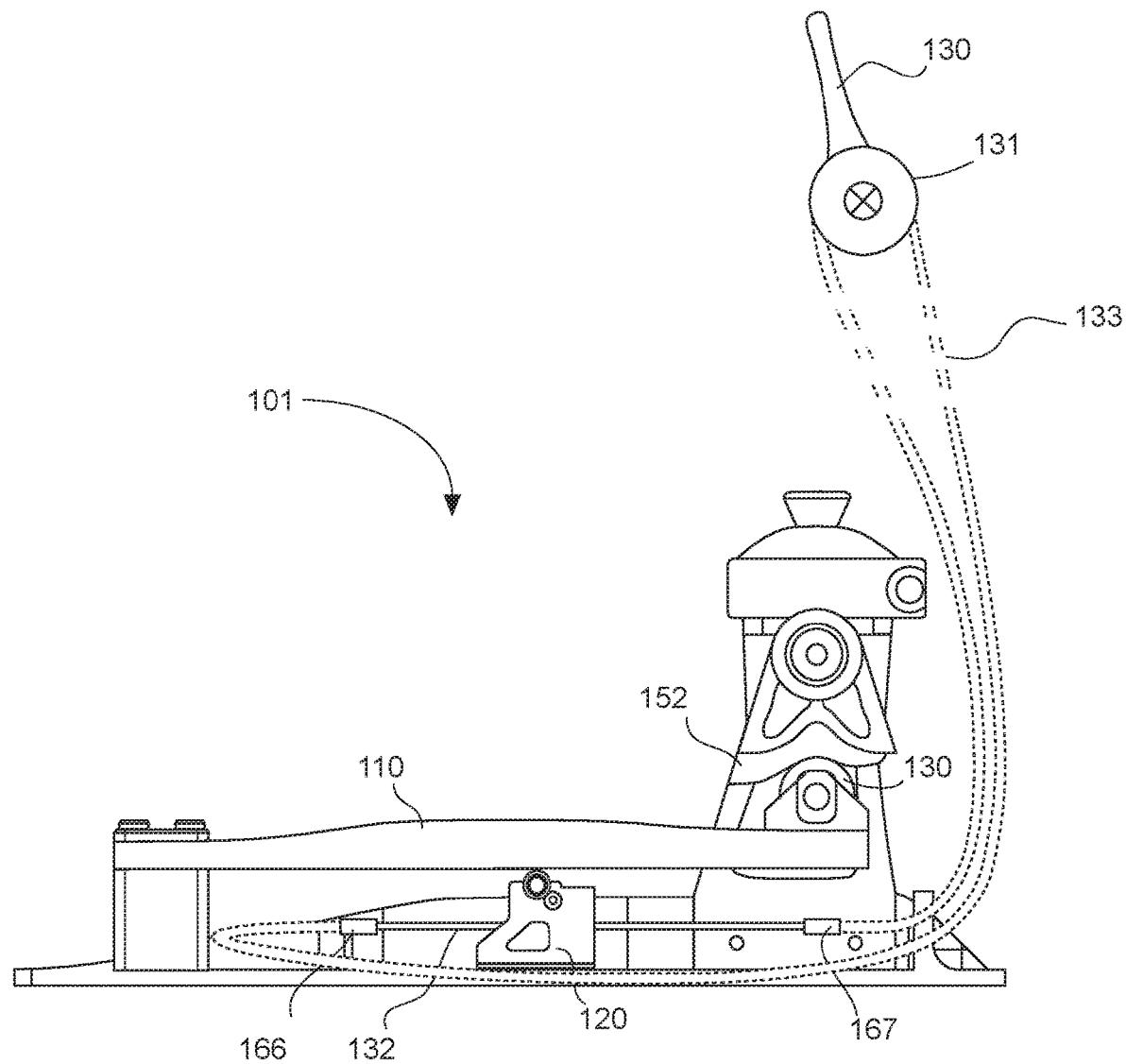
FIG. 10 displays a side view of an example passive ankle prosthesis.

FIG. 10 displays a side view of an exemplary ankle prosthesis 101. The prosthesis 101 employs several of the same designs as in prosthesis 201, including the cam-based transmission, its lightweight aspect, its ability to fit into an anthropomorphic physical envelope, and the design of a cam profile.

The prosthesis 101 comprises a lever transmission that permits the modification of the slider position by hand, circumventing the need for the small electric motor to adjust the position of the slider 120. As shown in FIG. 10, the lever transmission comprises a lever 130, a pulley block 131, a cable 132, a cable covering 133, and slider stoppers 166. Adjustment of the position of the lever 130 moves the slider along and beneath the leaf spring 110, which in turn, changes the ankle mechanics. At specific positions of the lever 130, the foot mechanics will change appropriately for different mobility tasks. For example, the lever transmission may include a lever setting for each task, including walking, standing, stair ascent/descent, and ramp ascent/descent. The lever 130 may be mounted anywhere for ease of access. For example, the lever 130 may be mounted on the ankle prosthesis 101, on the prosthetic pylon, on the socket, or on another location that the user can quickly and easily access throughout the day. The lever transmission enables movement of the slider, thereby allowing the user to change the ankle mechanics. For example, adjusting the position of the lever 130 causes the cable 132 to move around the pulley block 131. The slider 120 is affixed to a position on the cable 132 so that movement of the cable 132 causes the slider 120 to move along the length of the cable 132 between distal stopper 166 and proximal stopper 167.

In an exemplary prosthesis, the lever may comprise a Bowden cable transmission that adjusts the slider position. A Bowden cable transmission, which is similar to a bicycle cable, may be preferred due to the flexibility of lever location, simplicity, and robustness. The specific lever and Bowden cable implementation can be configured based on the distance needed to travel (about 6 cm), and the desired rotational range of the lever. The diameter of the cable can be minimal, since there is very little friction between the slider and the prosthesis frame due to the Teflon pads.

Figure 11:
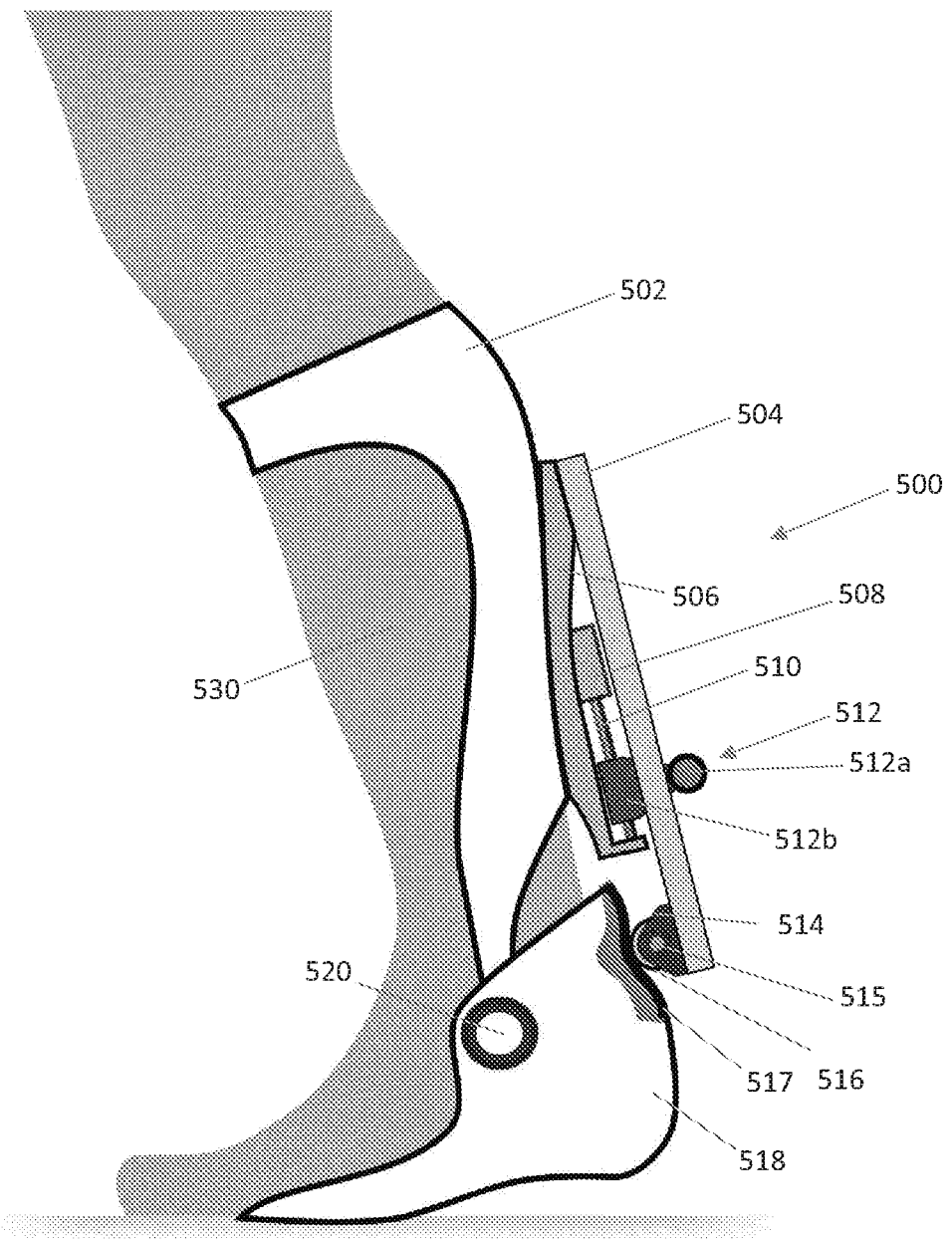
FIG. 11 displays a side view of an example orthosis.

The use of a leaf spring system to assist in gait may be incorporated into other assistive devices, such as orthoses. For instance, an orthosis 500 is shown in FIG. 11 that provides support to a leg 530. The orthosis 500 comprises an upper brace 502, and a lower brace 518 coupled by a pivotable connector 520 that serves as an artificial ankle joint of the orthosis 500. A support member 506 may be attached to the upper brace 502 and a leaf spring 504. A motor 508 drives a screw 510, and a slider 512 comprising an outer portion 512*a* and an inner portion 512*b* is adjustable along at least a portion of the length of the screw 510. The leaf spring 504 is attached at its end with an encasement 514, encasing a cam follower 516 that rolls along a profile 517 while the orthosis 500 is in use during gait of the leg 530. The cam transmission comprising the cam follower 516 and the profile 517 enables a customizable nonlinear torque-angle curve. The shape of the profile 517 may be determined by using a mathematical approach based on the principle of virtual work as described above. As shown in FIG. 11, the shape of the profile 517 is curved and includes a concave portion in which the cam follower 516 is positioned while the orthosis is in an equilibrium position, and convex portions along which the cam follower 516 rolls while the orthosis 500 is assisting with plantarflexion and dorsiflexion. The slider 512 provides sliding support to shift this curve to be more or less stiff overall. In other examples, the cam transmission could be housed on the anterior, lateral, or posterior side of the shank of the orthosis. Integration of the cam transmission into an orthosis such as the orthosis 500 can improve gait and a range of other mobility tasks for a broad spectrum of patients using orthoses, such as stroke, spina bifida, multiple sclerosis, and incomplete spinal cord injury.

What is claimed is:

1. A cam system for an assistive device, comprising:
a cam comprising at least two distinct cam profiles; and
a cam follower, wherein said cam follower is stationary, and
wherein said cam and said cam follower are configured to switch between said distinct cam profiles when the assistive device is in use.

2. The cam system of claim 1, wherein said distinct cam profiles are distinct adjacent cam profiles or a cam surface with continuous cam profiles.

3. The cam system of claim 1, wherein said cam comprises a cam profile slider and a stationary component, wherein said cam profile slider is configured to move relative to said stationary component.

4. The cam system of claim 3, wherein said cam profile slider moves in the medio-lateral direction.

5. The cam system of claim 3, wherein said cam profile slider comprises a top surface and a bottom surface.

6. The cam system of claim 1, wherein said bottom surface comprises said at least two distinct cam profiles.

7. The cam system of claim 1, wherein said bottom surface contacts said cam follower.

8. The cam system of claim 1, wherein said distinct cam profiles each comprise a transition zone and a distinct zone.

9. The cam system of claim 7, wherein said cam profile slider switches between said adjacent cam profiles when the transition zones of said distinct cam profiles are aligned.

10. The cam system of claim 9, wherein said switching is passive or via a transport component configured to move said cam profile slider.

11. The cam system of claim 10, wherein said transport component is selected from the group consisting of a plurality of magnets, a solenoid, a pneumatic component, and a linkage component.

12. The cam system of claim 1, wherein said cam follower is a roller.

13. The cam system of claim 1, wherein each of the at least two distinct cam profiles comprises a cam surface comprising a slope.

14. The cam system of claim 13, wherein the cam follower is positioned to roll along, and is switchable between, the cam surfaces of the at least two distinct cam profiles.

15. The cam system of claim 13, wherein each of the at least two distinct cam profiles comprise a discrete path.

16. The cam system of claim 15, wherein the discrete path comprises a groove provided within the cam profile.

17. The cam system of claim 13, wherein the cam follower is positioned to roll along, and is switchable between, the discrete paths of each of the at least two distinct cam profiles.

18. A cam system for an assistive device, comprising:
a cam comprising a cam profile slider component comprise at least two distinct cam paths and a stationary component; and
a cam follower, wherein said cam follower is stationary, and
wherein said cam profile slider switches between said distinct adjacent cam paths when the assistive device is in use.

19. A cam system for an assistive device, comprising:
a cam comprising at least two distinct adjacent cam profiles; and
a cam follower configured to switch between said distinct adjacent cam profiles when the assistive device is in use wherein said cam follower is stationary.

* * * * *